(12) United States Patent
Wu

(10) Patent No.: US 10,791,923 B2
(45) Date of Patent: Oct. 6, 2020

(54) BALL LENS FOR OPTICAL PROBE AND METHODS THEREFOR

(71) Applicant: Canon U.S.A., Inc., Melville, NY (US)

(72) Inventor: Tzu-Yu Wu, Malden, MA (US)

(73) Assignee: Canon U.S.A., Inc., Melville, NY (US)

(*) Notice: Subject to any disclaimer, the term of this patent is extended or adjusted under 35 U.S.C. 154(b) by 0 days.

(21) Appl. No.: 16/577,445

(22) Filed: Sep. 20, 2019

(65) Prior Publication Data

US 2020/0093365 A1    Mar. 26, 2020

Related U.S. Application Data

(60) Provisional application No. 62/735,618, filed on Sep. 24, 2018.

(51) Int. Cl.
| | |
|---|---|
| G02B 6/00 | (2006.01) |
| A61B 3/10 | (2006.01) |
| G02B 6/32 | (2006.01) |
| G02B 6/26 | (2006.01) |

(Continued)

(52) U.S. Cl.
CPC .......... *A61B 3/102* (2013.01); *A61B 5/0066* (2013.01); *G01B 9/0205* (2013.01); *G01B 9/02091* (2013.01); *G02B 6/262* (2013.01); *G02B 6/32* (2013.01)

(58) Field of Classification Search
CPC ..... A61B 3/102; A61B 5/0066; A61B 5/0084; G02B 6/32; G02B 6/262; G01B 9/02091; G01B 9/0205
See application file for complete search history.

(56) References Cited

U.S. PATENT DOCUMENTS

| | | |
|---|---|---|
| 6,433,937 B1 | 8/2002 | Konno |
| 6,445,939 B1 | 9/2002 | Swanson et al. |
| 6,501,878 B2 | 12/2002 | Hughes et al. |

(Continued)

FOREIGN PATENT DOCUMENTS

WO    2015116939 A1    8/2015

OTHER PUBLICATIONS

Bélanger, P.A, "Beam propagation and the ABCD ray matrices", Opt. Lett., Feb. 15, 1991, pp. 196-198, vol. 16, No. 4.

(Continued)

*Primary Examiner* — Ellen E Kim
(74) *Attorney, Agent, or Firm* — Canon U.S.A., Inc., IP Division

(57) ABSTRACT

An optical probe includes first and second light guiding components, and a ball lens arranged along an optical axis and enclosed in a sheath having asymmetric optical power. The probe transmits at least two light beams including first and second beams each having a different wavelength. The ball lens has a curved surface and an angled surface arranged such that light is reflected off from the angled surface and focused by the curved surface at a working distance with a beam waist profile having lateral and longitudinal directions. Beam waist locations of the first and second beams are different from each other, and the beam waist profiles of the first and second beams in the lateral direction differs less than the beam waist profiles in the longitudinal direction. This ball lens design compensates for the sheath asymmetric optical power and provides balanced astigmatism and substantially achromatic performance.

33 Claims, 20 Drawing Sheets

(51) Int. Cl.
*G01B 9/02* (2006.01)
*A61B 5/00* (2006.01)

(56) References Cited

U.S. PATENT DOCUMENTS

| | | | |
|---|---|---|---|
| 6,564,089 B2 | 5/2003 | Izatt et al. | |
| 6,904,197 B2 * | 6/2005 | Bhagavatula | G02B 6/2552 |
| | | | 385/31 |
| 7,366,376 B2 | 4/2008 | Shishkov et al. | |
| 7,680,378 B2 | 3/2010 | Alphonse et al. | |
| 7,705,992 B2 | 4/2010 | Hatori et al. | |
| 7,813,609 B2 | 10/2010 | Petersen et al. | |
| 7,920,271 B2 | 4/2011 | Vakoc et al. | |
| 8,180,134 B2 | 5/2012 | Wang | |
| RE43,875 E | 12/2012 | Shishkov et al. | |
| 8,515,221 B2 | 8/2013 | Flanders et al. | |
| 8,582,934 B2 | 11/2013 | Adler et al. | |
| 8,676,013 B2 | 3/2014 | Bouma et al. | |
| 8,781,287 B2 | 7/2014 | Flanders et al. | |
| 8,928,889 B2 | 1/2015 | Tearney et al. | |
| RE45,512 E | 5/2015 | Tearney et al. | |
| 9,036,966 B2 * | 5/2015 | Bhagavatula | G01B 9/02035 |
| | | | 385/33 |
| 9,069,122 B2 | 6/2015 | Takeuchi et al. | |
| 9,087,368 B2 | 7/2015 | Tearney et al. | |
| 9,164,272 B2 | 10/2015 | Maillard et al. | |
| 9,318,810 B2 | 4/2016 | Zelenski | |
| 9,332,942 B2 | 5/2016 | Jaffer et al. | |
| 9,364,167 B2 | 6/2016 | Vertikov | |
| 9,557,154 B2 | 1/2017 | Tearney et al. | |
| 10,048,454 B2 * | 8/2018 | Fiebig | G02B 6/4214 |
| 10,234,676 B1 | 3/2019 | Elmaanaoui | |
| 2003/0095746 A1 | 5/2003 | Williamson | |
| 2005/0165315 A1 | 7/2005 | Zuluaga et al. | |
| 2006/0067620 A1 | 3/2006 | Shishkov et al. | |
| 2007/0233396 A1 | 10/2007 | Tearney et al. | |
| 2008/0013960 A1 | 1/2008 | Tearney et al. | |
| 2009/0190883 A1 * | 7/2009 | Kato | A61B 5/0073 |
| | | | 385/33 |
| 2009/0262361 A1 * | 10/2009 | Tanioka | A61B 5/6852 |
| | | | 356/479 |
| 2009/0306477 A1 | 12/2009 | Togino | |
| 2009/0323076 A1 | 12/2009 | Li et al. | |
| 2011/0137124 A1 | 6/2011 | Milner et al. | |
| 2011/0141759 A1 | 6/2011 | Smith | |
| 2012/0101374 A1 | 4/2012 | Tearney et al. | |
| 2014/0180083 A1 | 6/2014 | Hoseit | |
| 2015/0378105 A1 | 12/2015 | Godbout et al. | |
| 2016/0228071 A1 | 8/2016 | Wang et al. | |
| 2016/0274345 A1 | 9/2016 | Ueno et al. | |
| 2016/0299170 A1 | 10/2016 | Ito et al. | |
| 2017/0168232 A1 | 6/2017 | Tearney et al. | |
| 2017/0209049 A1 | 7/2017 | Wang et al. | |
| 2018/0070932 A1 | 3/2018 | Tearney et al. | |
| 2018/0303327 A1 | 10/2018 | Yamada | |
| 2019/0223699 A1 | 7/2019 | Wu | |
| 2019/0223700 A1 | 7/2019 | Wu | |
| 2019/0227297 A1 | 7/2019 | Wu | |
| 2019/0227298 A1 | 7/2019 | Elmaanaoui | |

OTHER PUBLICATIONS

Wang, T., et al, "Numerical analysis of astigmatism correction in gradient refractive index lens based optical coherence tomography catheters", Applied Optics, Jul. 20, 2012, pp. 5244-5252, vol. 51, No. 21.

Benalcazar, W. A., et al, "Aberration characterization for the optimal design of high-resolution endoscopic optical coherence tomography catheters", Optics Letters, Mar. 15, 2012, pp. 1100-1102, vol. 37, No. 6.

Yuan, W., et al, "Super-achromatic monolithic microprobe for ultrahigh-resolution endoscopic optical coherence tomography at 800nm", Nature Communications.

* cited by examiner

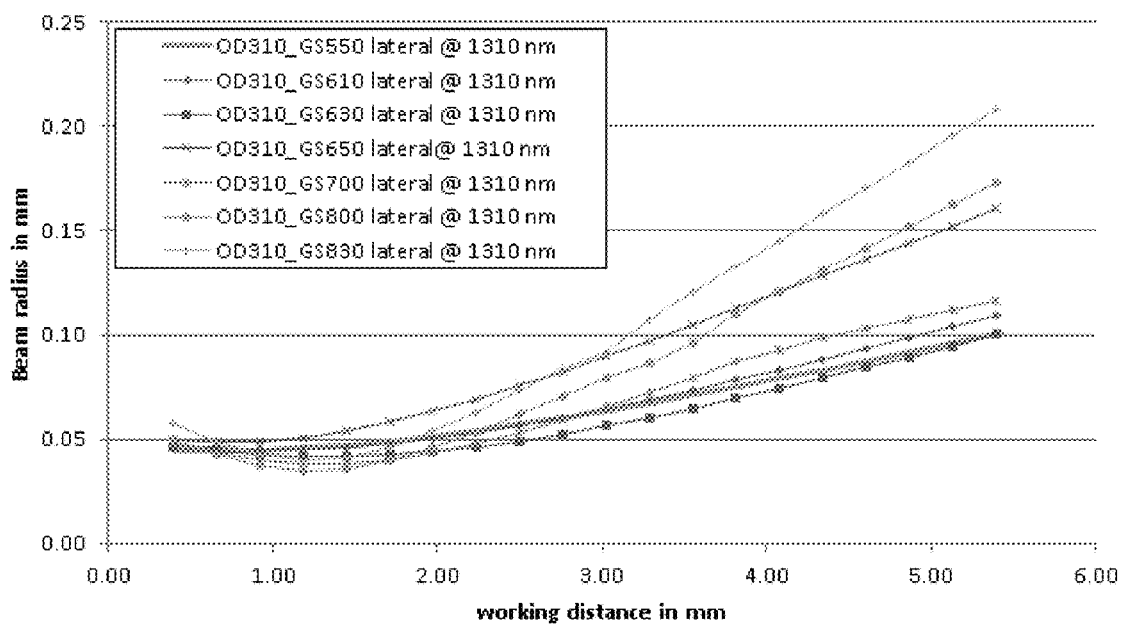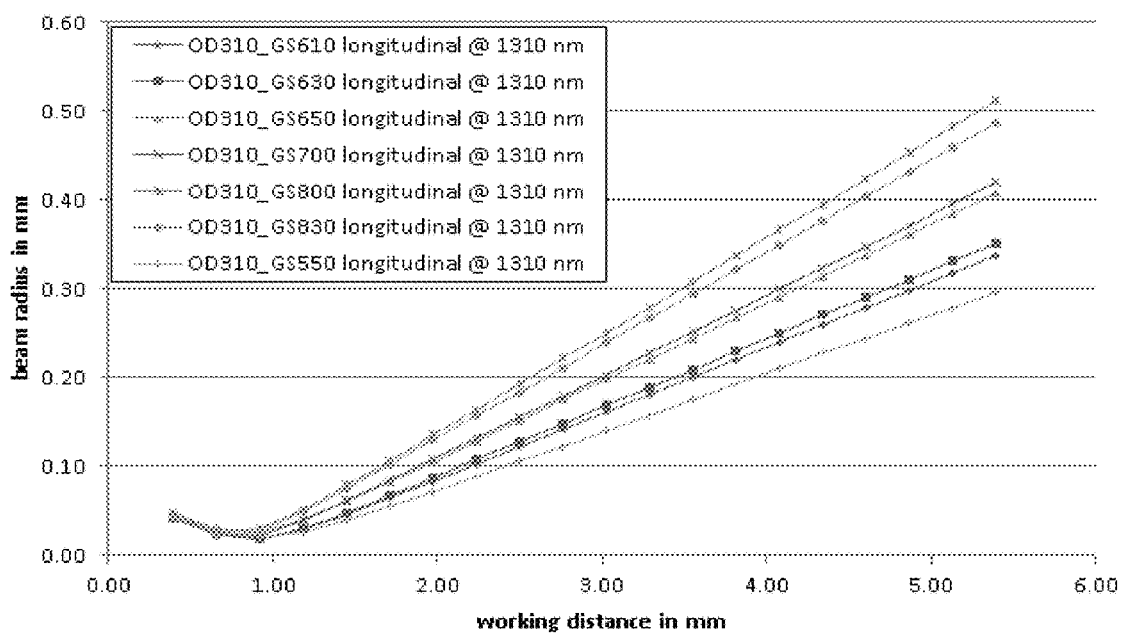

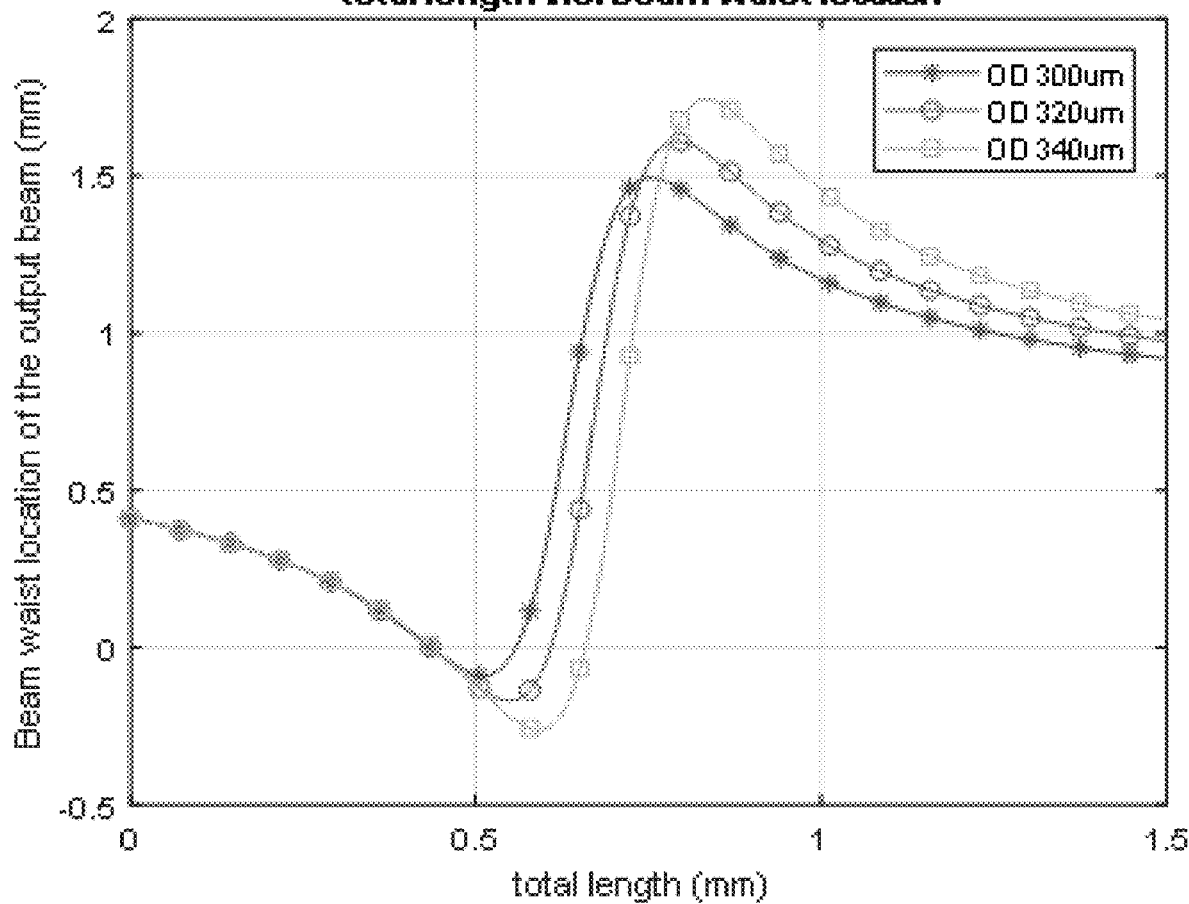

FIG. 26A
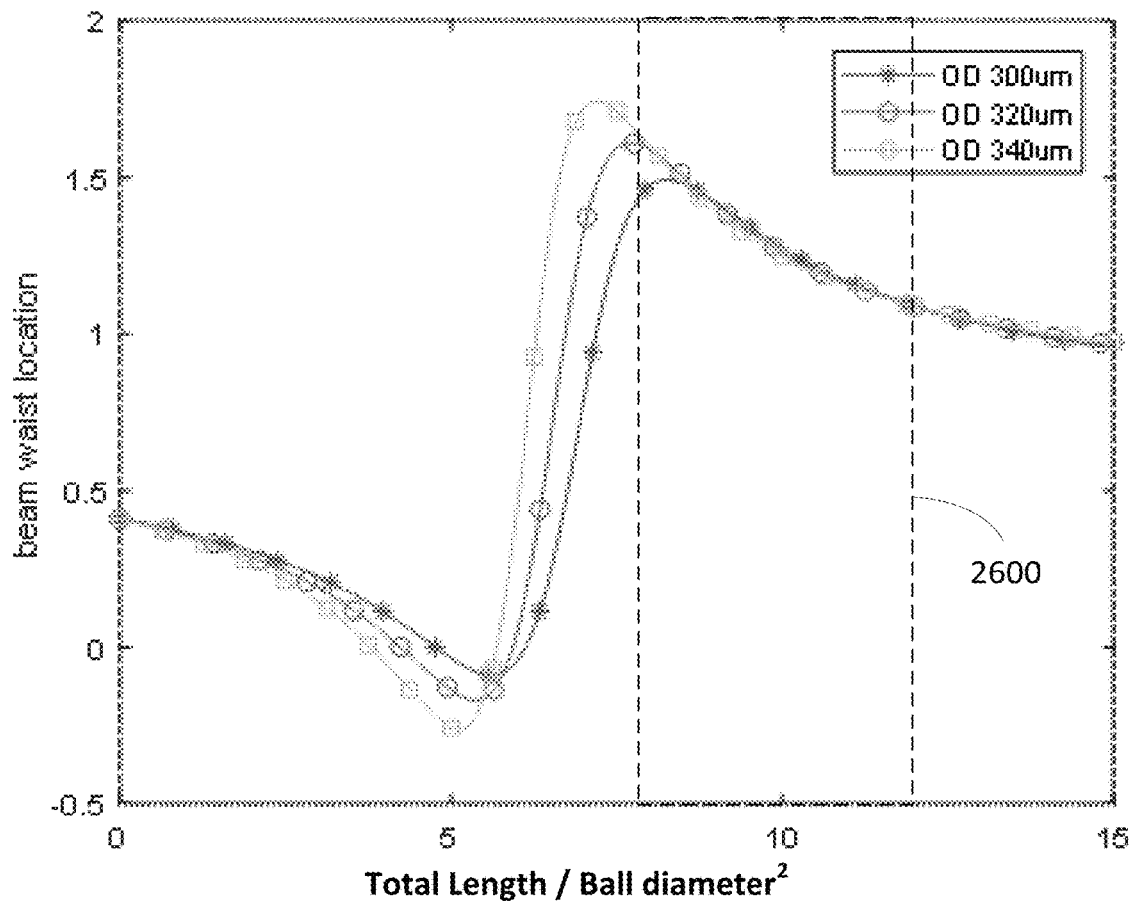
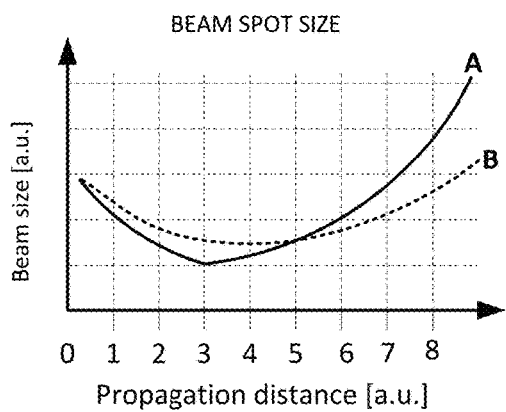
FIG. 26B
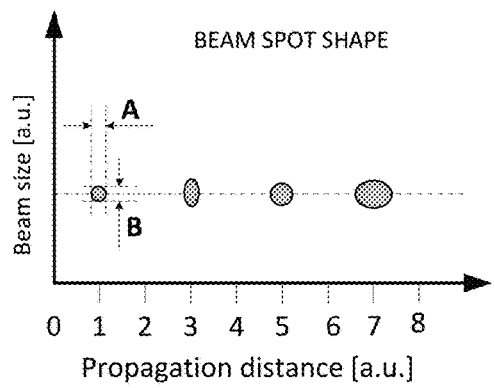
FIG. 26C rc >> R

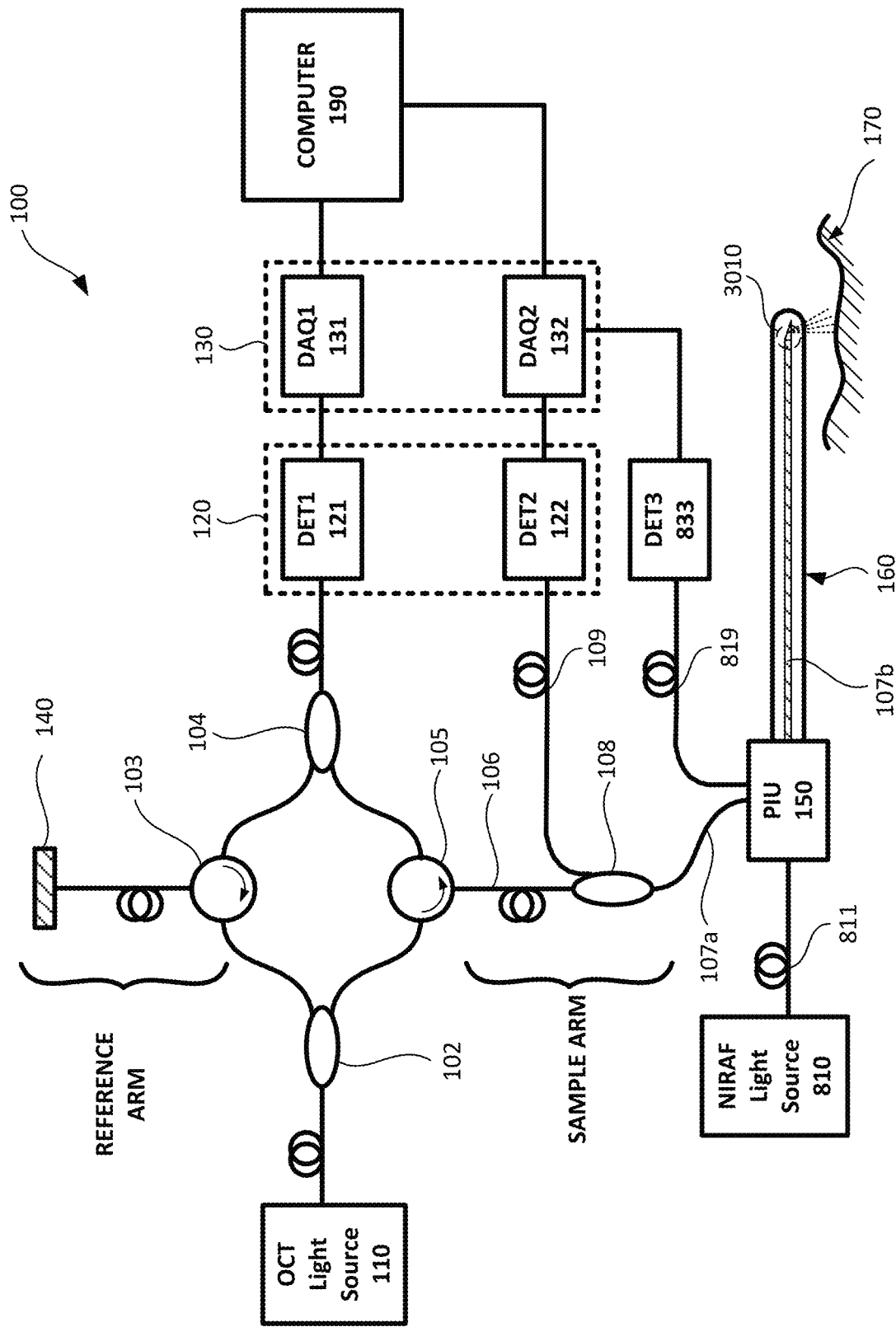

LONGITUDINAL VIEW

LATERAL VIEW

BALL LENS FOR OPTICAL PROBE AND METHODS THEREFOR

CROSS-REFERENCE TO RELATED APPLICATIONS

The present application claims priority to U.S. provisional application 62/735,618, filed Sep. 24, 2018, the disclosure of which is incorporated by reference herein in its entirety.

BACKGROUND INFORMATION

Field of the Disclosure

The present disclosure generally relates to medical devices. More particularly, the disclosure describes examples of ball lens design for distal optics of an optical probe. In some preferable embodiments, the ball lens design provides advantageous achromatic performance for multimodality optical coherence tomography (OCT) imaging systems.

Description of Related Art

Fiber based OCT catheters are widely used in medical imaging to obtain depth-resolved images of bodily lumens, such as vessels, for biomedical analysis and medical diagnosis. The catheter, which generally comprises a sheath, a coil and an optical probe, is navigated to a coronary artery, by manual or automated control. In order to acquire cross-sectional images of bodily lumens and natural cavities such as vessels, the esophagus, a nasal cavity, etc., the optical probe of a catheter is rotated with a fiber optic rotary joint (FORJ). In addition, the optical probe is simultaneously moved (translated) longitudinally during the rotation so that images are obtained in a helical scanning pattern. This longitudinal movement is most commonly performed by mechanically pulling the tip (distal end) of the probe back towards the proximal end and therefore this process is referred to as a "pullback" operation.

FIG. 31A and FIG. 31B respectively illustrate transverse and axial views of conventional distal optics 12 (optical probe) of a catheter 20 at sequential positions during a pullback operation. With reference to FIG. 31A, a sample beam 10 emitted from distal optics 12 of the catheter 20 scans the inner surface 14 of a bodily lumen 15 (i.e., a sample, e.g., an artery). The catheter 20 rotates or oscillates (as indicated by arrow 16) about its own axis Ox, while being pulled back inside a sheath 30 which remains stationary. In this manner, the catheter 20 can continuously sweep the sample beam 10 in a rotary fashion (shown in FIG. 31B) through successive radial directions, and collects back-reflected light, which carries information about the illuminated inner surface 14 (e.g., tissue). An interference signal of the back-reflected light is obtained by combining the reflected light of the sample beam to with a reference light beam (not shown). The interference signal is converted into an electronic signal, digitized, stored, and/or processed to analyze the status of the sample being examined.

The combination of backscattered light from the sample beam to and reference light from the reference beam (not shown) results in the interference signal, only if light from both the sample and reference beams have traveled substantially the same optical distance (where "substantially the same optical distance" indicates a difference of less than or equal to the coherence length of the light source). Regions of the sample 15 that reflect more light will create stronger interference signals than regions that reflect less light. Any light that is outside the coherence length will not contribute to the interference signal. The intensity profile of the reflected light, referred to as an A-scan or A-scan line, contains information about the spatial dimensions and location of structures within the sample. An OCT image (i.e., a cross-sectional tomograph generally referred to as a B-scan) may be formed by combining multiple adjacent A-scans at different transverse positions. The diagram of FIG. 31A depicts positions (a plurality of transversal locations T1, T2, T3, T4) of the catheter 20 at corresponding timings t1, t2, t3, t4, along the pullback path, while scanning the sample 15 with light of the sample beam to at a fixed (same) axial angle θ. Delta (δ) is the distance the catheter travels during pullback in between successive measurements (A-scans).

The rotational movement 16 of the catheter 20 enables A-lines to be generated for multiple radial directions each corresponding to a circumferential position on the inner surface 14. Combining the plurality of A-line scans allows the generating a 2D image of a cross section of the sample. Each 2D image of an artery cross section, for example, may be formed by approximately 500 lines or more, corresponding to a full circumferential (360 degree) scan by the catheter 20. This full circumferential scan may be sometimes referred to as a frame. Three-dimensional (3D) imaging of the inner surface 14 can be achieved by combining plural 2D image frames obtained during the longitudinal translational motion of the pull-back operation while the catheter is rotating. The resulting catheter scan is a helical path of successive A-lines to form a full 3D dataset of the inner surface 14 of the sample 15. Each 360 degree rotation scan within the helical path may also be referred to as a frame, and multiple frames are generated along the longitudinal (z) axis. Data collected from successive A-line scans is processed (e.g., by fast Fourier transformation and other known algorithms) to generate OCT images of the sample 15 in a known manner.

The distal optics of a catheter is usually fragile and therefore it is protected by a transparent tubular sheath and a metallic tube (metallic can) with a transparent window integrally fixed (welded) to the distal end of the sheath. The sheath is commonly made of medical-grade flexible optical transparent plastic such as Fluorinated Ethylene Propylene (FEP) or Polyethylene (PE). The sheath isolates the tissues under investigation from the rotating catheter parts, and protects the catheter inside from mechanical damage and/or bodily fluids or contrast agents. However, while effectively protecting the optical probe from mechanical damage or fluids, the tubular sheath acts as a negative cylindrical (concave/convex) lens, contributing to uneven divergence of the light beam in at least one direction. Specifically, optical aberration in the form of astigmatism is introduced to the optical system due to the cylindrical shape of the sheath and/or tube. Astigmatism causes foci of the beams in two orthogonal directions to fall at different distances with different beam sizes and results in degradation of image quality.

FIG. 32A and FIG. 32B respectively illustrate transverse (longitudinal) and axial (lateral) views of conventional distal optics 12 (optical probe) of a catheter 20 with the focusing effects caused by the tubular shape of the sheath 30. FIG. 32C and FIG. 32D show exemplary graphs of the irradiance profile of an astigmatic beam.

In FIG. 32A, n1 is the refractive index of the inner medium, n2 is the refractive index of the sheath's material, n3 is the refractive index of the outer medium, and Wyz is the focusing distance of beam to in the longitudinal direction (i.e., along the YZ plane). In FIG. 32B, Wyx is the focusing distance of the beam to in the lateral direction along the YX plane. As illustrated by the diagrams of FIGS. 32A and 32B, due to the defocusing effect of the tubular sheath 30 (in the lateral direction the sheath 30 acts as a cylindrical lens), the focusing distance Wyx in the azimuthal or lateral direction is shifted by an amount ΔW with respect to the focusing distance Wyz in the lateral direction along the YZ plane. FIG. 32C shows how the beam spot size diverges as function of the propagation distance. Specifically, as shown in FIG. 32C, the beam spot size in the azimuthal or lateral direction (represented by line A) is initially smaller than the beam spot size in the longitudinal direction (represented by line B). However, as the beam 10 propagates through the sheath 30 and farther away from the probe optical axis, the beam spot size in the longitudinal direction (line B) becomes larger than the spot size in the lateral direction. FIG. 32D illustrates how the beam shape changes as function of propagation distance. As shown in FIG. 32D, the shape of the beam spot is initially very narrow in the lateral direction (value of A) and wide in the longitudinal direction (value of B). However, as the beam propagates through the sheath and away from the probe optical axis, the shape of the beam spot becomes larger (wider) in the lateral direction than in the longitudinal direction. As the spot expands in the lateral direction, the energy of the spot spreads from the center to the periphery, which reduces the irradiance peak value. The lower irradiance peak value reduces the magnitude of the impulse response (point spread function) in the lateral direction, and thus leads to degradation in image quality. See, for example, Wang et al., "Numerical analysis of astigmatism correction in gradient refractive index lens based optical coherence tomography catheters", Applied Optics 51(21):5244-52, July 2012.

One approach to overcome astigmatism has been to match the index of refraction of the sheath with the medium outside and inside of the sheath. Another approach to reduce astigmatism is to minimize the thickness of the sheath. In addition, several distal optical designs have been proposed to compensate astigmatism including some designs using additional optical components or surfaces that have asymmetric optical power. See, for example, U.S. Pat. Nos. 9,069,122, 8,582,934, 7,366,376, RE45512, RE43875, 6,445,939, and 10234676. However, these approaches generally increase complexity of the catheter design, make the catheter more vulnerable to damage (e.g., by reducing the thickness of the sheath), add difficulty for assembling and alignment of the optical core, and tend to increase the final cost of the system as a whole.

In addition, in newer optical catheters it is beneficial to integrate other imaging modality to an OCT system such as combining fluorescence imaging to detect vulnerable plaque by exciting and detecting the auto-fluorescent signal from the blood vessel tissues and plaques. In such multi-modality OCT (MMOCT) system, the distal optics not only needs to overcome the optical degradation from astigmatism introduced by the sheath, but it also needs to correct chromatic aberration caused by the wavelength difference between OCT wavelength and fluorescence excitation and detection wavelengths.

The application of endoscopic catheters in a liquid environment further aggravates the astigmatism because the spot size in the azimuthal or lateral direction increases quickly with increasing refractive index of the outer medium. As noted above, the current state of the art has been primarily focused on correcting astigmatism such that the beam waist profile in the azimuthal direction matches the beam waist profile in the longitudinal plane. However, in practice, equalizing the beam waist profile in the azimuthal direction to match the profile in the longitudinal plane has proven to be costly and difficult.

SUMMARY OF EXEMPLARY EMBODIMENTS

According to at least one embodiment of the present disclosure, there is provided an exemplary optical probe which avoids or at least mitigates the above-discussed issues of astigmatism and chromatic aberrations, to thereby improve image quality in an MMOCT system. According to the various embodiments disclosed herein, fully correcting astigmatism perfectly may not be desirable or necessary, because the data sampling rate in OCT imaging is different in the two orthogonal directions. Therefore, a small amount of astigmatism can be allowed without adding image degradation. The inventor herein has identified that by bringing the foci of the two orthogonal directions close enough so that the beam will not be significantly diverging in one direction while the other direction is converging, image degradation can be suppressed and the optical design of the probe can be simplified. As a result, it is possible to provide a cost effective solution to the issues of astigmatism and chromatic aberration.

According to one embodiment, an optical probe includes a first light guiding component, a second light guiding component, and a ball lens arranged along an optical axis of the optical probe. A sheath encloses the optical probe. The optical probe is used to deliver light with at least two different wavelengths to the distal tip of the probe and to collect light with at least two different wavelength ranges. A first beam having OCT wavelength is used for OCT imaging and a second beam having excitation wavelength for fluorescence is used for fluorescence imaging. The ball lens has a predetermined diameter and an angled surface at angle ø such that the light is reflected off from the angled surface by total internal reflection and/or by a mirror coating on the angled surface. Then the reflected light is focused by the curved surface of the ball lens at a working distance with a predetermined beam waist profile. The beam waist locations between the beam having OCT wavelength and the beam having excitation wavelength are within a minimum difference in lateral and longitudinal directions. The ball lens design provides balanced astigmatism and substantially achromatic performance between 633±10 nm and 1310 nm without adding additional optical component with asymmetric optical power to compensate the asymmetric optical power from the sheath.

According to another embodiment, an optical probe for multi-modality optical coherence tomography (MMOCT) imaging of a bodily lumen, includes: a first light guiding component; a second light guiding component; and a ball lens arranged in this order from a proximal end to a distal end along an optical axis of the probe, wherein the probe is configured to deliver light with at least two different wavelengths to the distal end of the probe and to collect light with at least two different wavelength ranges, wherein the ball lens has a curved surface and an angled surface arranged such that the light is reflected off from the angled surface by total internal reflection and/or by a mirror coating on the angled surface, and the reflected light is focused by the curved surface at a working distance, wherein, when measured perpendicularly from the optical axis, a beam waist location in a lateral direction is further than a beam waist location in a longitudinal direction, and wherein a beam waist profile in the lateral direction is substantially the same as a beam waist profile in the longitudinal direction.

According to a further embodiment, an imaging apparatus for multi-modality optical coherence tomography (MMOCT) imaging of a bodily lumen, comprises: an optical probe including a first light guiding component, a second light guiding component, and a focusing component arranged in this order from a proximal end to a distal end along an optical axis of the probe; and a sheath surrounding the probe, wherein the probe is configured to deliver light of at least two different wavelengths and to collect light with at least two different wavelength ranges for side-view imaging through the sheath, wherein the focusing component includes a focusing surface and a reflecting surface, the reflecting surface is oriented at an angle to the optical axis such that the light is reflected from the reflecting surface to the focusing surface by total internal reflection and/or by a mirror coating on the angled surface, and the reflected light is focused as a beam at a working distance substantially perpendicular to the optical axis, and wherein the beam expands in a lateral direction and in a longitudinal direction with substantially a same beam waist profile in both directions.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

FIG. 11 is a graph showing a beam profile of a 310 μm OD ball lens (in contrast with sheath) with various glass spacer lengths in lateral direction.

FIG. 12 is a graph showing a beam profile of a 310 μm OD ball lens (in contrast with sheath) with various glass spacer lengths in longitudinal direction.

FIG. 25 is a graph showing exemplary optical probe total length vs. beam waist location relation modeled by lens formula with Gaussian properties.

FIG. 26A is a graph illustrating the relation between beam waist location in lateral direction and the ratio x defined by Equation 3. FIG. 26B and FIG. 26C are graphs illustrating a relation of beam spot profile as a function of propagation distance.

FIG. 30 illustrates an exemplary multi modality OCT (MMOCT) system.

Figure 1A:
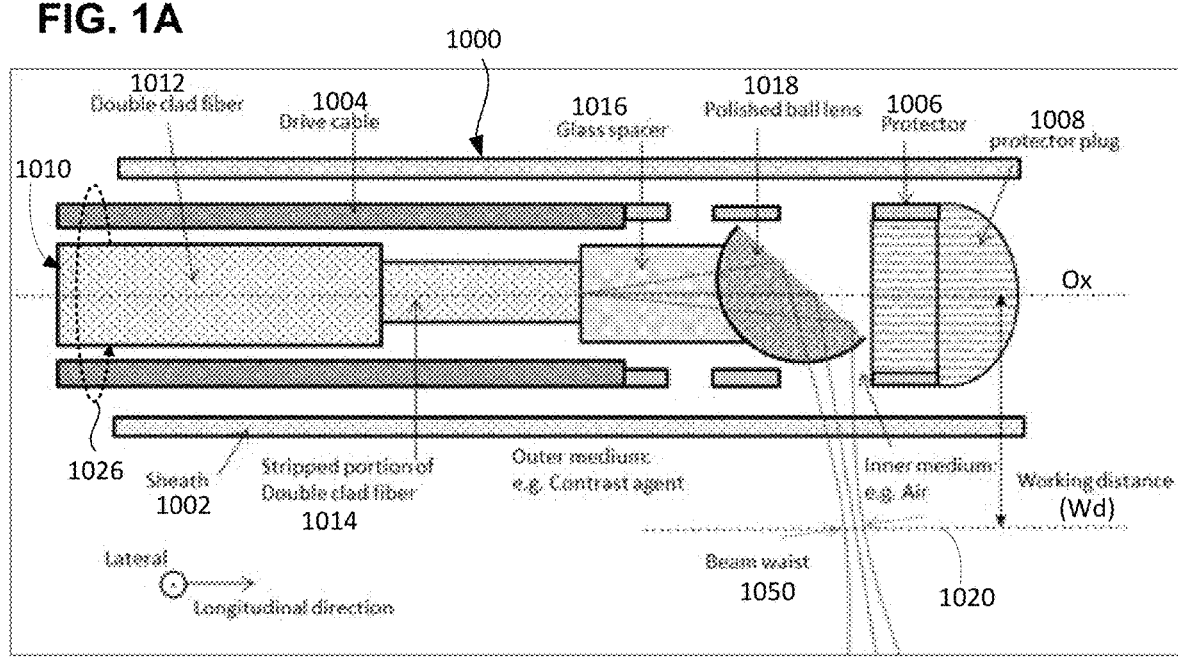
FIG. 1A shows an exemplary embodiment of an imaging catheter assembly having a ball lens at the distal end thereof.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled" or the like to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown in one embodiment can apply to other embodiments. It will also be appreciated by those of skill in the art that references to a structure or feature that is disposed "adjacent" to another feature may have portions that overlap or underlie the adjacent feature.

DETAILED DESCRIPTION OF EXEMPLARY EMBODIMENTS

The present disclosure generally relates to medical devices, and it exemplifies embodiments of a probe for multi-modality optical coherence tomographic (OCT). The embodiments of the OCT probe and portions thereof are described in terms of their state in a three-dimensional space. As used herein, the term "position" refers to the location of an object or a portion of an object in a three-dimensional space (e.g., three degrees of translational freedom along Cartesian X, Y, Z coordinates); the term "orientation" refers to the rotational placement of an object or a portion of an object (three degrees of rotational freedom—e.g., roll, pitch, and yaw); the term "posture" refers to the position of an object or a portion of an object in at least one degree of translational freedom and to the orientation of that object or portion of the object in at least one degree of rotational freedom (up to six total degrees of freedom); the term "shape" refers to a set of posture, positions, and/or orientations measured along the elongated body of the object. As it is known in the field of medical devices, the terms "proximal" and "distal" are used with reference to the manipulation of an end of an instrument extending from the user to a surgical or diagnostic site. In this regard, the term "proximal" refers to the portion of the instrument closer to the user, and the term "distal" refers to the portion of the instrument further away from the user and closer to the surgical or diagnostic site.

As used herein the term "catheter" generally refers to a flexible and thin tubular instrument made of medical grade material designed to be inserted through a narrow opening into a bodily lumen (e.g., a vessel) to perform a broad range of medical functions. The more specific term "optical catheter" refers to a medical instrument comprising an elongated bundle of one or more flexible light conducting fibers disposed inside a protective sheath made of medical grade material and having an optical imaging function.

The embodiments are based on the object of providing improved distal optics for a multi-modality OCT probe. In all embodiments, the distal optics consists of a ball lens designed to provide advantageous achromatic performance and reduced astigmatism.

The requirement for multimodality OCT (MMOCT) for cardiovascular applications use will be as follows. Two beams are transmitted through and exit from a single optical fiber; the fiber can be a multi-clad fiber (e.g., a double clad fiber). One beam (a first beam) is used for OCT imaging, and for a preferred embodiment the OCT beam has a central wavelength of about 1310 nanometers (nm). The OCT wavelength can be broadband or can be scanned for the bandwidth of about 100 nm to 150 nm. The other beam (a second beam) has the wavelength of excitation of autofluorescence of a given sample. For human tissue, the second beam has wavelength of about 633±10 nm.

The detection wavelength for fluorescence is between 670-870 nm and the fluorescent signal is collected by the 1st clad of the double clad fiber. The incidence angle of the beam to the inner surface of sheath needs to be greater than to degrees and less than 30 degrees in air. The beam waist location of the focused beam is between 0.5 to 3 millimeters (mm) measured perpendicularly away from the optical axis of the fiber/spacer for the OCT and fluorescence wavelengths.

Astigmatism is balanced for the focused beams of the OCT and fluorescence imaging. Chromatic aberration is at least partially corrected between 1310 nm and 633±10 nm. The focused beam for the fluorescence beam needs to focus outside of the sheath.

In catheter-based optical coherence tomography (OCT), image resolution is determined primarily by the optical beam characteristics and the sampling rates in both pullback direction (longitudinal direction) and the scanning direction (lateral direction). While the light beam suffers astigmatism introduced by the sheath, which causes foci of the beams in two orthogonal directions falling in different distances with different beam sizes, sampling rates in two orthogonal directions are also different in normal OCT operation. As an example of OCT operational settings: 500 A-lines per frame; 40 mm/s pull-back speed with 200 frames per second (fps), the sampling size is 0 to 63 microns (μm) for an imaging depth from 0 to 5 mm in scanning (lateral direction), and is about 200 μm in pull-back (longitudinal direction). As a result of different sampling sizes in two orthogonal directions, the optical beam characteristics are allowed to differ in two directions based on the Nyquist sampling theorem without degrading the overall resolution. In particular, the beam performance in pull-back/longitudinal direction is more forgiving than the one in scanning direction due to the much coarse sampling size.

The present disclosure describes the design parameters and exemplary ball lens designs that provide "balanced" performance in the two directions without complicating the distal optics design and without introducing additional optical components with asymmetric optical power to compensate for astigmatism from the sheath. In the present disclosure, "balanced performance" means that the designs take advantage of different sampling sizes in OCT imaging and optimize the beam profile in the scanning (or lateral) direction more than the one in pull-back (or longitudinal) direction, while controlling the astigmatism such that the image quality of OCT is not limited by the resolution of the distal optics throughout most of the OCT imaging depth (most of the depth of field range). As for fluorescence imaging, it is contemplated advantageous to have the beam characteristics (e.g., beam waist location and divergence angle) of the excitation beam to be similar to that of OCT beams, but provide larger numerical aperture (NA) for the detection beams in order to increase the detection efficiency.

A fully astigmatism corrected OCT probe may be disadvantageous for fluorescence collection because OCT distal optics is normally designed to have very small NA to achieve better depth of focus and sensitivity throughout the entire imaging depth. As a result of different nature and requirements for excitation and detection in fluorescence imaging, fluorescence imaging also allows astigmatism to be present but controlled. The optimization preference in fluorescence imaging is given to the excitation beam in lateral direction to be similar to OCT beam while it allows the beams in longitudinal direction diverging faster to have larger NA for better collection efficiency.

With the balanced performance described above, this present disclosure also provides the design parameters and exemplary ball lens designs that provide achromatic performance for a multimodality OCT system primarily operating at OCT wavelength of 1310 nm and fluorescence excitation wavelengths of 633±10 nm. It should be noted that throughout the present disclosure, the term "longitudinal direction" is also referred to as the pull-back direction, and similarly the term "lateral direction" is also referred as the scanning direction. Accordingly, these terms may be interchangeably used through the present disclosure.

The remainder of the present disclosure is organized as follows:

A first section presents an overview of a catheter configuration including an optical probe which uses the novel distal optics which is part of the subject of the present disclosure. A second section describes more in detail an exemplary embodiment of a ball lens probe with a sheath. A third section provides design specifications, design method and model for achieving balanced astigmatism. A fourth section describes a design method and model for achieving achromatic performance between 1310 nm and 633 nm wavelength with balanced astigmatism. Sections 5th, 7th, 9th, 11th and 13th provide exemplary embodiments of specific ball lens probe designs. Sections 6th, 8th, 10th, 12th and 14th provide exemplary embodiments of specific ball lens probe designs with an acceptable range of glass spacer length. A 15th section describes a design method for determining glass spacer length range for a specific ball lens diameter using a specified range for a ratios of (Total length)/(Ball diameter)$^2$.

1st Embodiment

In a first embodiment the present disclosure provides a catheter including a novel distal optics assembly. FIG. 1A illustrates a partially-cutaway view of an example embodiment of an imaging catheter 1000, which consists of a sheath 1002, a coil or drive cable 1004, a protector 1006, a protector plug 1008, and an optical probe 1010. The drive cable 1004, protector 1006 and protector plug 1008, and the optical probe 1010 are rigidly fixed relative to each other. The drive cable 1004 delivers torque from the proximal end to distal tip of the optical probe 1010 so that a distal tip of the optical probe can rotate or oscillate in direction of arrow 1026 to see an omnidirectional view of the inner surface of a bodily lumen or hollow organ 1020.

The sheath 1002 remains stationary and contains thereinside the rotating protector plug 1008, the protector 1006, and drive cable 1004. The rotating protector 1006 surrounds part of the optical probe 1010, and contains an inner medium (e.g., air). The sheath 1002 is surrounded by an outer medium (e.g., contrast agent or bodily fluid such as blood), which is the medium outside the sheath. The optical probe 1010 includes, from the proximal end to the distal end arranged along an optical axis Ox, a multi-clad fiber 1012, a stripped portion 1014 of a multi-clad fiber, a spacer 1016, and a ball lens 1018. The ball lens 1018 has a curved surface 1020 and an angled surface 1030 arranged such that the light is reflected off from the angled surface 1030 and is focused by the curved surface 1020 at a working distance (Wd) with a same beam waist profile whether the beam is observed in the lateral direction or the longitudinal direction. That is, the ball lens (a focusing component) includes a focusing surface and a reflecting surface, the reflecting surface is oriented at an angle to the optical axis such that the light is reflected from the reflecting surface to the focusing surface, and thereafter the light is focused in a lateral direction and in a longitudinal direction with a same beam waist profile in both directions.

Figure 1B:
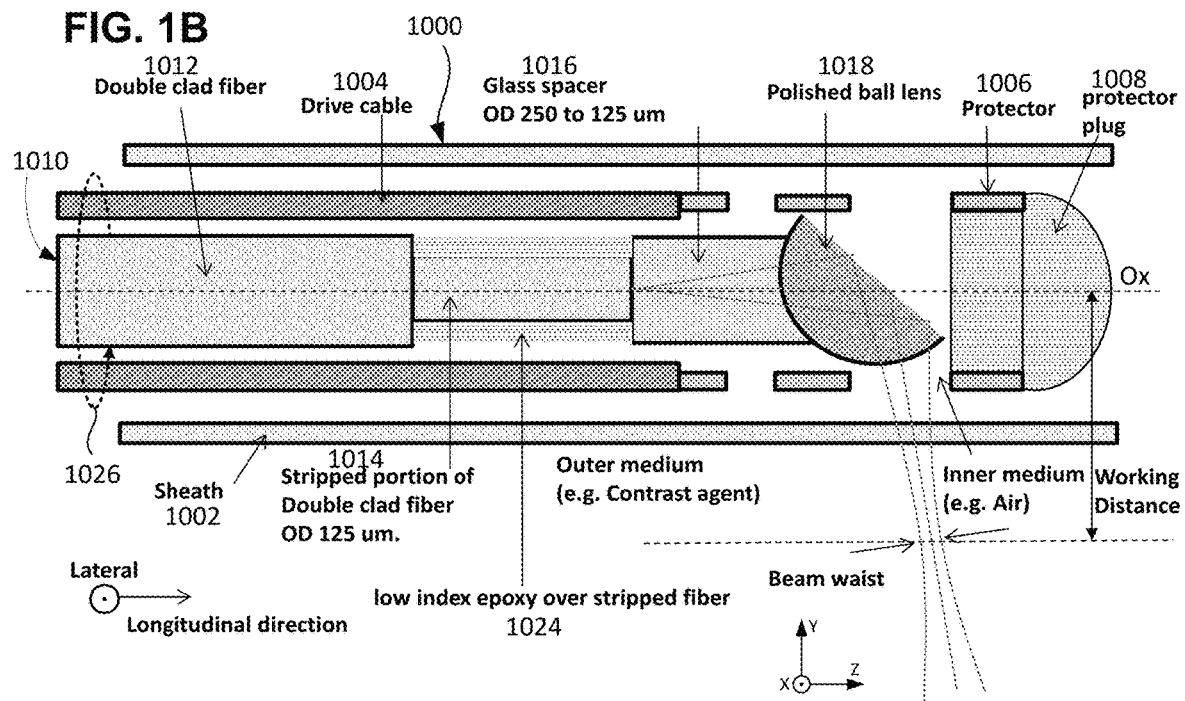
FIG. 1B shows some specific parameters of the exemplary embodiment of an imaging catheter assembly having a ball lens at the distal end thereof.

FIG. 1B illustrates an exemplary embodiment of a catheter 1000 including a novel distal optics assembly similar to that of FIG. 1A. In the embodiment of FIG. 1B, the optical probe 1010 similarly includes, from the distal end to the distal end along the axis Ox, a multi-clad fiber 1012, a stripped portion 1014 of a multi-clad fiber 1012, a spacer 1016, and a ball lens 1018. In FIG. 1B, the stripped portion 1014 of the multi-clad fiber is covered with a low refractive index epoxy material 1024.

2nd Embodiment

Figure 2A:
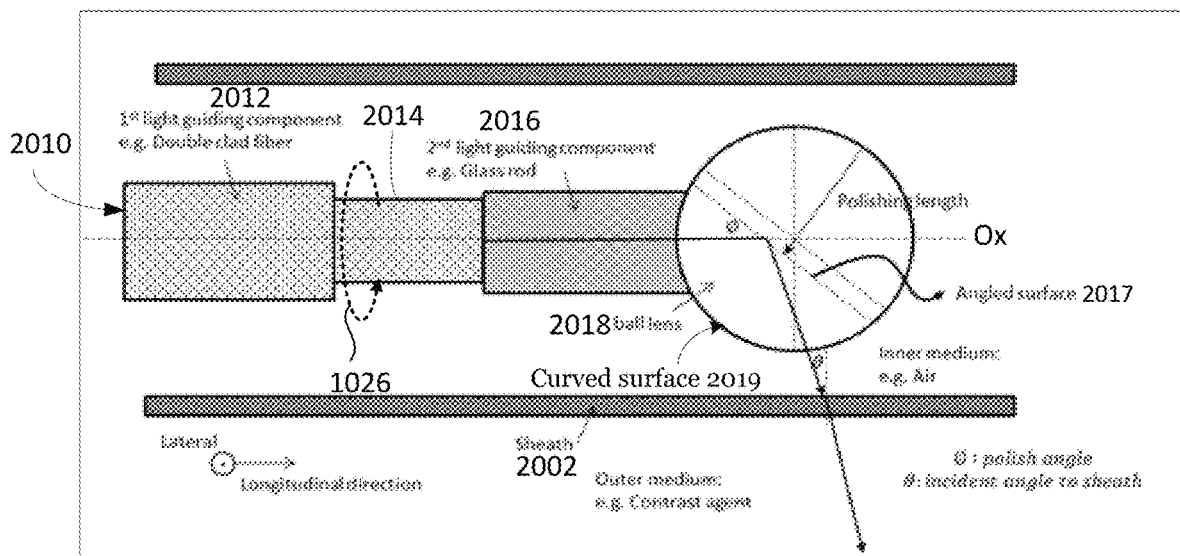
FIG. 2A and FIG. 2B show exemplary parameters for a ball lens optical probe.
Figure 2B:
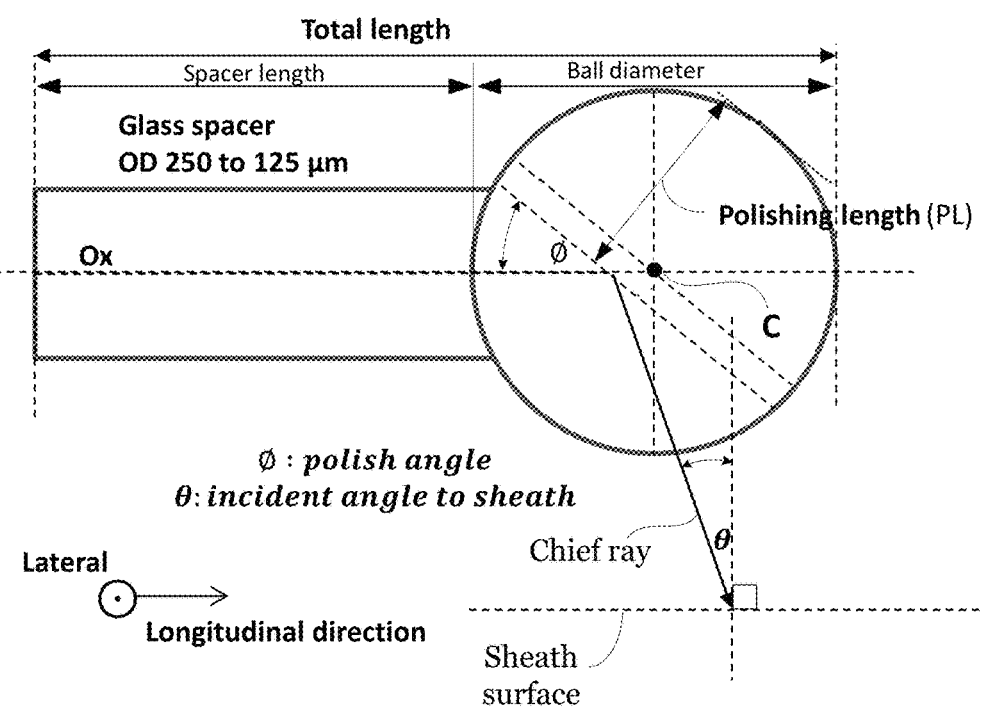

FIG. 2A illustrates an exemplary embodiment of a ball lens optical probe 2010 disposed inside a sheath 2002, but without showing the drive cable for ease of illustration. FIG. 2B illustrates an exemplary embodiment of design parameters of a ball lens optical probe. Specifically, FIG. 2A illustrates a partially-cutaway view of an example embodiment of the ball lens optical probe. The optical probe 2010 shown in FIG. 2A includes a first light guiding component 2012 (e.g., a single mode fiber, a double clad fiber or a multimode fiber), a stripped portion 2014 of the first light guiding component, a second light guiding component 2016 (e.g., fused silica glass spacer, a coreless fiber, or cylindrical rod made of optical grade polymers), and a ball lens 2018. The ball lens 2018 has a substantially spherical shape where a sphere formed by a fusion lens forming procedure from the 2nd light guiding component, or the sphere may be fabricated separately and then shaped by glass polishing and grinding. The ball lens 2018 may also be monolithically formed with the second light guiding component by 3D printing or other fabrication methods. An example of ball lens microprobe formed by a fusion lens forming procedure from a multi-mode fiber was described by Wu Yuan et al., in "Super-achromatic monolithic microprobe for ultrahigh-resolution endoscopic optical coherence tomography at 800 nm", published by Nature Communications, November 2017, which is incorporated by reference.

The optical probe 2010 is used to deliver light with at least two different wavelengths from the proximal end to the distal tip of the probe, while at the same time rotating and collecting light with at least two different wavelength ranges. When the optical probe is used in a MMOCT system, one beam (a first beam) is used for OCT imaging and for some preferred embodiments it has the central wavelength of 1310 nm (OCT wavelength). The OCT wavelength can be broadband or can be scanned for the bandwidth of about 100 nm to 150 nm. The other beam (a second beam) has the wavelength of excitation for fluorescence (excitation wavelength). In an embodiment, the second beam is used for fluorescence of tissue and has the excitation wavelength centered at 633±10 nm. In collecting or receiving light of at least two different wavelengths, one of the received lights (a first collected light) is from the reflection and scattering of the OCT beam and has the same wavelength range as the incident OCT beam. The other of the received lights (a second collected light) is the excited auto-fluorescent signal from a sample irradiated by the excitation wavelength. The auto-fluorescent signal has a wavelength range between 670-870 nm. That is, the second collected light has a wavelength different from the wavelength of the first beam and different from the wavelength of the second beam.

In some embodiments, the ball lens has an outer diameter (OD) ranging from 290 to 350 μm assuming the ball lens is sphere made of fused silica and is fabricated (angle polished) with an angled surface 2017 with a obtuse angle ø such that the light is reflected off from the angled surface 2017 by total internal reflection and/or a mirror coating on the angled surface. The reflected light is thereafter incident on a curved surface 2019. The obtuse angle ø is referred herein as the "polishing angle"; it is an angle formed by the angled surface with respect to the optical axis (Ox) of the optical probe. The polishing length (indicated in FIG. 2A and FIG. 2B as a distance PL) is slightly over or under the radius of the ball lens to reduce back-reflection from the angled surface. In an embodiment, the ratio of the ball lens radius to the polishing length is in the range of 0.85-0.95 for over polishing, and is between 1.05-1.18 for under polishing. Note that the fabrication method of a ball lens probe is not limited to forming a spherical ball lens from a fusing splicing procedure followed by angle polishing. As long as the ball lens parameters of the curved surface 2019 and angled surface 2017 are met, any method of manufacture can be used to make the ball lens 2018. In some embodiments, the ball lens probe can be fabricated by alternative methods such as injection molding or 3D micro-optics printing.

The polishing length and polishing angle indicated in FIGS. 2A and 2B are used to describe geometrical dimensions of the ball lens probe, but term "polishing" does not limit the fabrication method of the ball lens probe. That is, the fabrication of the ball lens is not limited to the polishing method. For example, in the case of 3D printing or injection molding, the geometrical shape of the ball lens probe would be established beforehand and fabricated directly with the desired radius, angle of inclination of the angled surface, etc. In this case, the angled surface can be constructed with an appropriate finish, e.g., with a reflective coating, so there would be no need to have additional polishing. Nevertheless, the terms radius/diameter, polishing length and polishing angle indicated in FIGS. 2A and 2B still apply.

Furthermore, an optical imaging device may include a transparent sheath that encloses the optical probe. The sheath has an inner diameter in the range of 500 μm-650 μm, an outer diameter in the range of 700-850 μm and a refractive index of about 1.53. In some preferred embodiments, the sheath has an inner diameter of 584±12.7 μm and an outer diameter of 787±12.7 μm.

The ball lens diameter, ball lens material, its polishing angle ø, the polishing length PL and the inner medium control an incident angle θ (an angle formed between a beam of light incident on the inner surface of the sheath and the normal to the sheath, as indicated in FIG. 2A). As shown in FIG. 2A, the incident angle θ is the angle of the chief ray to the inner surface of the sheath 2002 and the normal to the sheath. The incident angle θ in longitudinal direction is designed to be in the range of 10-25 degrees. In some preferred embodiments, the incident angle θ is at 20 degrees±4 degrees when the inner medium is air. Table 1 summarizes the parameters of an example for a 300 μm diameter ball lens design in which different incident angle θ is achieved by controlling the polishing length and polishing angle ø. In some preferred embodiments, the polishing angle ø is at 38 degrees and the polishing length is 170 μm for a 300 μm OD fused silica ball lens such that the incident angle θ to the sheath is at 19.6 degrees in an inner medium of air. To facilitate manufacturing and alignment, the center C of the ball lens 2018 is aligned with the optical axis Ox of the optical probe 2010.

TABLE 1 tabulates the corresponding incident angles θ of different polishing angles Ø and polishing lengths for a ball lens having OD = 300 μm

| Polishing length | Polishing angle Ø | | | | |
| --- | --- | --- | --- | --- | --- |
| | 35 | 36 | 37 | 38 | 39 |
| 130 | 14.2 | 12.3 | 10.3 | 8.4 | 6.5 |
| 140 | 17.2 | 15.2 | 13.2 | 11.3 | 9.3 |
| 150 | 20.0 | 18.0 | 16.0 | 14.0 | 12.0 |
| 160 | 22.8 | 20.8 | 18.8 | 16.7 | 14.7 |
| 170 | 25.8 | 23.7 | 21.7 | 19.6 | 17.5 |
| 175 | 27.4 | 25.3 | 23.2 | 21.1 | 19.0 |

Note:
Polishing length (left most column) is in units of micrometers (μm), and the polishing angle (top row) and incident angles (remainder of table) are in units of degrees.

The sheath may be a tubular member made of transparent or mostly transparent material, or the sheath may include a mostly-transparent window so that the beam of light can transmit through the sheath substantially unobstructed. Since the sheath has a cylindrical or tubular shape, it has optical power, although the optical power of the sheath is not very strong when the medium inside (inner medium) and the medium outside (outer medium) of the sheath are the same (e.g., the media inside and outside the sheath are both contrast agent). However, if the inner and outer media are different, then the sheath has a stronger asymmetrical optical power. For example, if the medium inside the sheath is air and the medium outside the sheath is a contrast agent, then the sheath has a negative optical power in the lateral or scanning direction. Additionally, the smaller the diameter of the sheath, the stronger the optical power of the sheath, and the greater the astigmatism caused by the sheath.

[3rd Embodiment] Design Specification and Method of Fabricating Ball Lens Probe with Balanced Astigmatism for OCT Imaging The present disclosure discloses the design method and exemplary ball lens designs that simplify the distal optics by balancing the optical powers for multimodality OCT imaging.

The optical performance specification for the "balanced performance" in the presence of astigmatism is listed in Table 2. As mentioned earlier, "balanced performance" means that the designs take advantage of different sampling sizes in OCT imaging and optimizes the beam profile in lateral (scanning) direction more than in longitudinal (pullback) direction while controlling the astigmatism such that the image quality of OCT is not limited by the resolution of the distal optics throughout most ranges of the OCT imaging depth.

TABLE 2

| Optical specifications for OCT imaging at 1310 nm wavelength | |
|---|---|
| Incident angle to the sheath in air | 20 ± 4 degrees |
| Divergence angle in lateral direction | 0.01-0.05 rad |
| Divergence angle in longitudinal direction | ≤0.12 rad |
| Beam waist location* in lateral direction | ≥1 mm |
| Beam waist location* in longitudinal direction | ≥0.5 mm |

Note:
In Table 2, *Beam waist location is measured perpendicularly from the optical axis (Ox) of the 1st and 2nd light guiding components (see FIG. 1B)

The design parameters for the ball lens probe are listed in Table 3:

TABLE 3

| Ball lens design parameters | | | | |
|---|---|---|---|---|
| Components | Parameters in ball lens design | | | |
| $2^{nd}$ light guiding component | Length (variable) | refractive index<br>n = 1.447 @ 1310 nm<br>n = 1.457 @ 633 nm | | |
| Ball lens | Radius (variable) | refractive index<br>n = 1.447 @ 1310 nm<br>n = 1.457 @ 633 nm | polishing angle Ø<br>38 degrees | polishing length<br>1.13 * ball<br>radius (variable) |
| Sheath | Inner diameter<br>584 μm | outer diameter<br>784 μm | refractive index<br>n = 1.5 @ 1310 nm<br>n = 1.51 @ 633 nm | |
| Inner medium | Air | | | |
| Outer medium | Contrast agent | | | |

In the following embodiments, the ball diameter and the length of $2^{nd}$ light guiding component (e.g., length of the glass spacer) are chosen to be variable to optimize the beam performance (e.g., beam waist location, beam size and divergence angle) while others are fixed throughout the design process. The parameters that are fixed are specified in numbers in Table 3 including refractive indices of $2^{nd}$ light guiding component (e.g., glass spacer), ball lens, sheath, outer and inner media, radii of sheath, and polishing angle. Since all the embodiments in the present disclosure are exemplary, the fixed parameters in Table 3 can still be modified based on different catheter designs, and the same design method described in the following sections is still applicable.

[Design Models]

Since the light source is a coherent light source and the beam performance is dominated by physical wave phenomena, the optimization is based on the simulation of Gaussian Beam Models and Physical Wave Propagation. As Gaussian Beam model has more assumptions and simplifications in the beam propagation theory, the simulation speed is faster but less accurate than the simulation done with Physical Wave Propagation.

Figure 3:
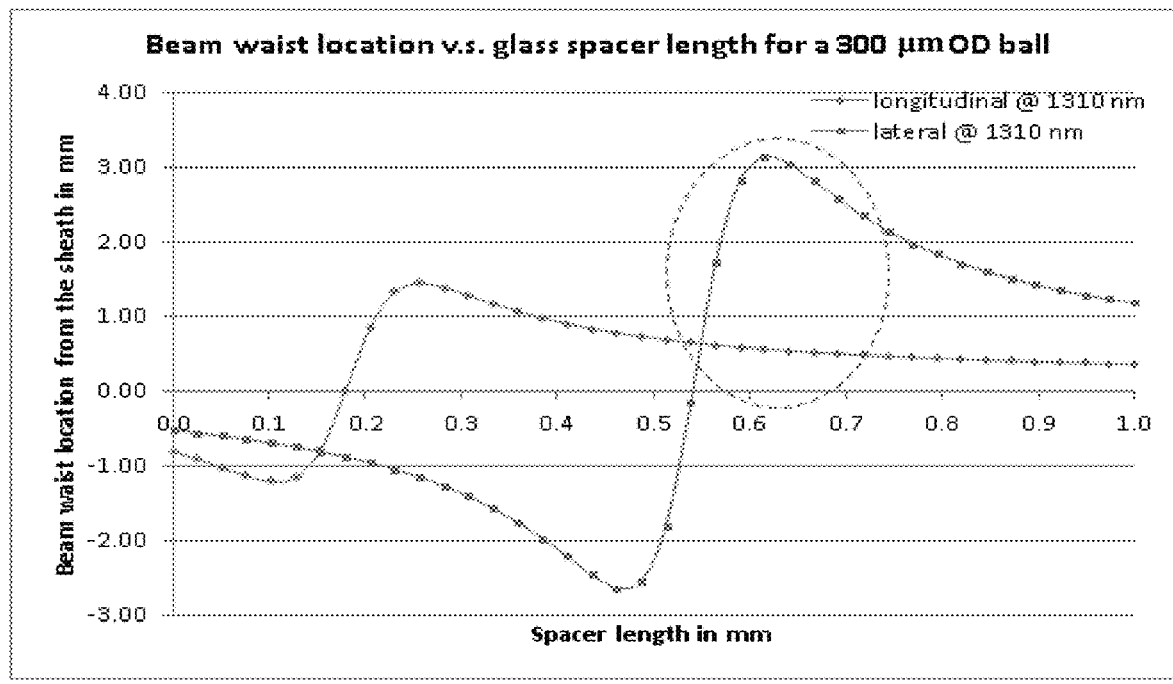
FIG. 3 is a graph showing beam waist location vs. glass spacer length simulated in Gaussian Beam model at wavelength=1310 nm for a 300 μm outer diameter (OD) ball lens (in contrast agent with sheath).
Figure 4:
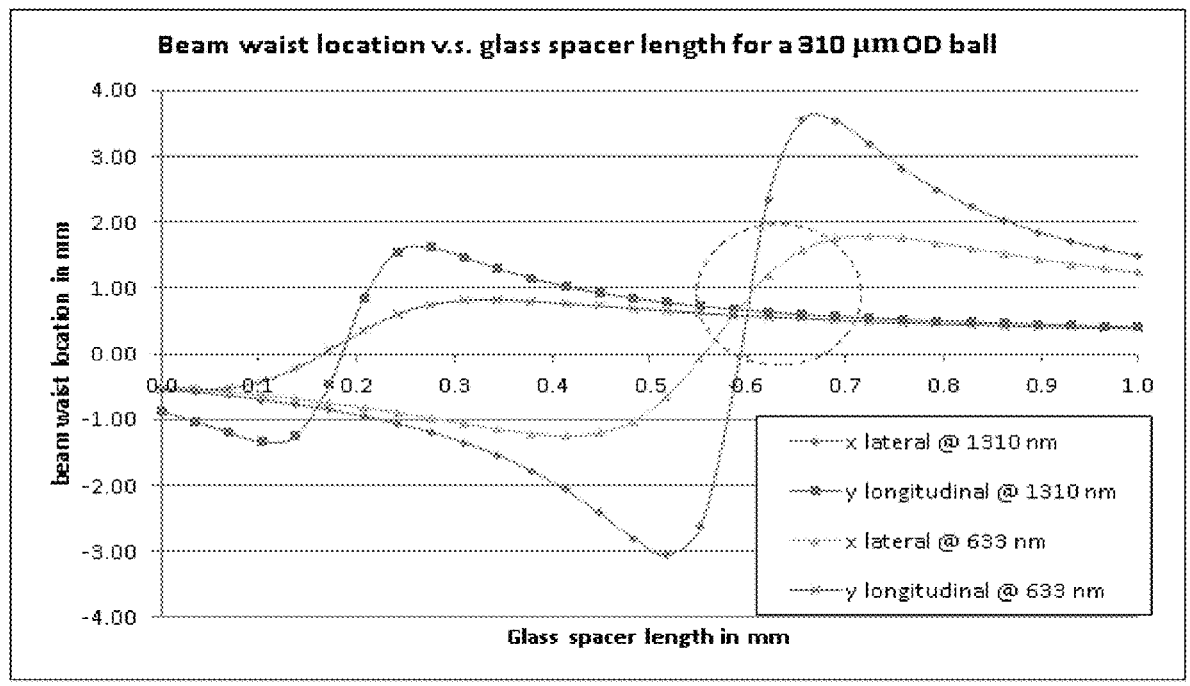
FIG. 4 shows an exemplary plot simulation in Gaussian Beam model of beam waist location vs. glass spacer length for an OD 310 μm ball lens probe (in contrast agent with sheath).

In the design process, a Gaussian Beam model is first used in the initial design phase to decide the range of glass spacer length for a certain ball lens diameter, followed by Physical Wave Propagation simulation to finalize the design configuration and determine the final performance. FIG. 3 and FIG. 4 show examples of Gaussian Beam modeling for determining beam waist location as function of spacer length.

[Design Method to Minimize Astigmatism]

To achieve minimum astigmatism and find the initial range for optimization, the present disclosure proposes to simulate the beam waist location vs. the length of $2^{nd}$ light guiding component (e.g., glass spacer length) for a given ball lens diameter in both lateral and longitudinal directions, and then find the intersection of the two curves and its vicinity as the starting values for the glass spacer length. If there is no astigmatism present, two curves of the two orthogonal directions should overlap with each other, but due to astigmatism introduced by the sheath, two curves shift away and only intersect at one point for the positive beam waist location. The intersection point is where the beam waist locations in the two orthogonal directions are close to each other, as predicted by the Gaussian Beam model (i.e. astigmatism is minimized).

FIG. 3 demonstrates an exemplary plot simulated in Gaussian Beam model of beam waist location vs. glass spacer length for a ball lens probe with OD 300 microns with other design parameters specified in Table 3. The plot of FIG. 3 suggests that astigmatism can be minimized by designing a glass spacer with a length around 550 μm for a 300 μm ball lens probe. While astigmatism may be minimized at or near the intersection point of the two curves, other optical specifications such as beam waist location and numerical aperture (NA) may not meet the requirement at the intersection point. It is important that the designer searches around the vicinity of the intersection point (shown as dashed circle in FIG. 3) such that the design meets all optical requirements with balanced astigmatism.

[4th Embodiment] Design Specification and Method for Achromatic Ball Lens Design with Balanced Astigmatism in Multimodality Imaging (OCT and Fluorescence Imaging)

In a multi-modality system in which OCT imaging is combined with fluorescence imaging, it is beneficial to design the distal optics, which is achromatic between the OCT operation wavelength (e.g., 1310 nm) and fluorescent excitation wavelength (e.g., 633±10 nm). The present disclosure proposes to minimize astigmatism and chromatic aberration simultaneously by at least the following steps.

1. Simulate and plot the relation between beam waist location vs. glass spacer length (i.e., the length of the second light guiding component) for a chosen ball diameter in both lateral and longitudinal directions, and at both the operational wavelengths (e.g., 1310 nm and 633±10 nm) to generate four curves. Due to chromatic aberration and astigmatism, the four curves are separated.

2. Find the intersection region of the four curves and use the corresponding glass spacer length as starting point for further ball lens optimization to achieve the final specification.

3. Fine tune (adjust) the spacer length around the intersection point (or intersection region) where the four curves meet to find the best performance that satisfies the desired specification.

4. Vary ball lens diameter and repeat steps 1-3 for each ball lens diameter to optimize the final performance.

FIG. 4 demonstrates an exemplary plot simulation in Gaussian Beam model of beam waist location vs. glass spacer length for an OD 310 μm ball lens probe with other design parameters specified in Table 3. The plot suggests that the astigmatism and chromatic aberration can be minimized simultaneously by designing a glass spacer length to be around 610 μm for a 310 μm OD ball lens without needing additional optical components.

The design methods mentioned in embodiments 3 and 4 are not limited to a ball lens optical probe design. For example, if a graded index (GRIN) lens is used instead of a ball lens, for a given length of GRIN lens (i.e. fixed optical power) one should follow the same design procedure to plot the relation between beam waist location vs. glass spacer length in two orthogonal directions and at the different wavelengths, and find the intersection region to determine the appropriate range for glass spacer length to minimize astigmatism without the need to introduce additional non-rotational symmetric component(s).

[5th Embodiment] Specific Ball Lens Design: OD 300 μm Ball Lens with Glass Spacer Length 550 μm In an embodiment, an exemplary ball lens has an outer diameter (OD) of 300 microns and is rigidly fixed to a glass spacer having a length of 550 microns. The ball lens optical probe design configuration parameters is shown in Table 4 and the simulation results is described in following:

TABLE 4

Ball lens probe configuration parameters

| Item | Material | Surface | Radius [mm] | Thickness [mm] |
|---|---|---|---|---|
| Light Source | — | 0 | Infinity | 0 |
| Glass spacer | Fused Silica | 1 | Infinity | 0.55 |

TABLE 4-continued

Ball lens probe configuration parameters

| Item | Material | Surface | Radius [mm] | Thickness [mm] |
|---|---|---|---|---|
| Ball lens | Fused Silica | 2 | Infinity | 0 |
|  | Fused Silica | 3 | Infinity | 300 μm OD |
|  | Fused Silica | 4 | 0.15 | ball with 170 μm polishing length at ⌀ = 38 degrees |
| Inner medium | Air | 5 | Infinity | 0.142 |
| Sheath | Polymer | 6 | 0.292 | 0.101 |
|  |  | 7 | 0.393 |  |
| Outer medium | Contrast agent | 8 | Infinity | Working distance |
| Imaging plane | Tissue | 9 | Infinity | — |

In an embodiment, light emits from a double clad fiber (the 1st light guiding component) with a NA 0.11 passing through a length of 550 μm glass spacer (2nd light guiding component) and then entering the ball lens having an OD of 300 μm. The ball lens is angle polished at polishing angle ⌀=38 degrees with a polishing length of 170 μm. Both the glass spacer and ball lens are made of fused silica.

In some embodiments, the ball lens is formed from the glass spacer by a fusion splicing ball lens forming procedure. In other embodiments, the ball lens is made by 3D printing with predefined polishing angle ⌀=38 degrees and polishing length of 170 μm, or alternatively ball lens is made by grinding and/or polishing a slab of fused silica. The tolerance of the ball lens diameter is ±3 μm.

The light is reflected by the angled surface of the ball lens by total internal reflection or by a reflective coating on the angled surface. The reflected light is focused by the curved surface of the ball lens. Light is incident on the inner surface of a sheath and then exits from the sheath. The sheath is considered to have negative optical power only in lateral direction.

The chief ray incident angle to the sheath in longitudinal direction is about 19.6 degrees in air.

In one embodiment the sheath has inner diameter of 0.584 mm and outer diameter of 0.787 mm (i.e., a thickness of about 200 microns), and is made of a material with refractive index of around 1.53. The sheath has air inside as the inner medium and contrast agent outside as the outer medium. The contrast agent has refractive index of about 1.45.

Figure 5:
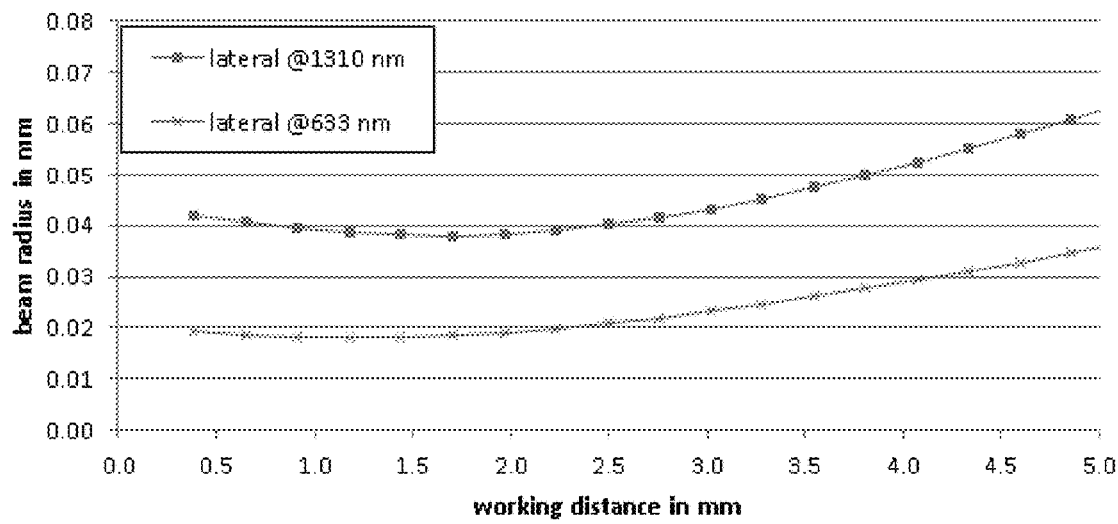
FIG. 5 shows a plot of beam profile (beam radius as a function of working distance) in lateral direction of a ball lens probe (in contrast agent with sheath) with 300 μm OD and 550 μm long glass spacer at 1310 nm and 633 nm wavelengths.
Figure 6:
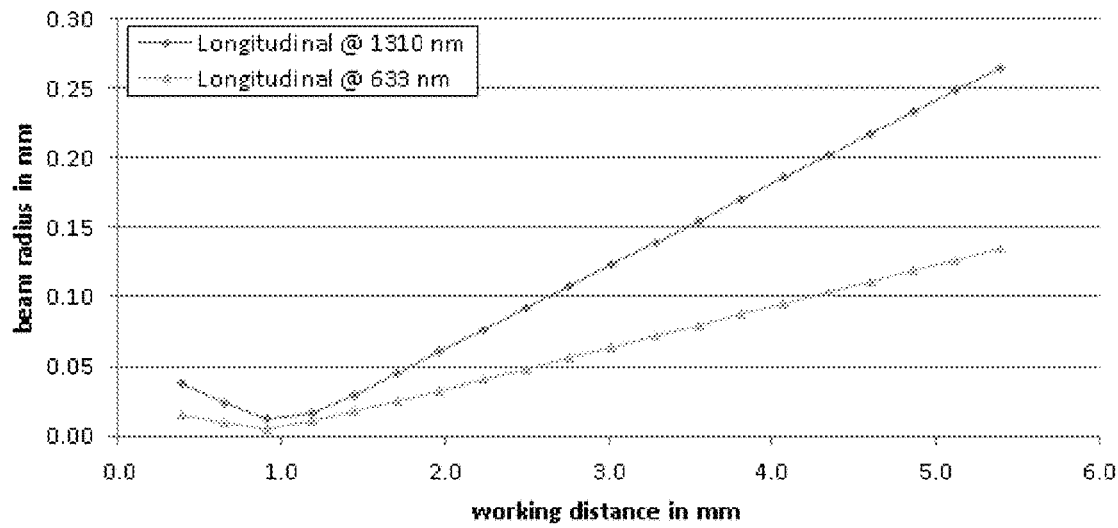
FIG. 6 shows a plot of beam profile (beam radius as a function of working distance) in longitudinal direction of a ball lens probe (in contrast agent with sheath) with 300 μm OD and 550 μm long glass spacer length at 1310 nm and 633 nm wavelengths.

FIG. 5 and FIG. 6 show exemplary beam profile plots simulated using Physical Wave Propagation model for the above design at 1310 nm and 633 nm wavelengths in lateral and longitudinal directions, respectively. As can be appreciated from FIG. 5, the plots demonstrate that the ball lens is substantially achromatic in both the lateral and longitudinal directions given that the beam waist locations between 1310 nm and 633 nm are within a 0.3 mm difference. As shown in FIG. 1B, the working distance is measured perpendicularly from the optical axis (Ox) of the 1st and 2nd light guiding components and the ball lens.

In the exemplary design, optimization preference is given to the beam performance in lateral (scanning) direction due to the much finer sampling rate in lateral direction than in longitudinal (pull-back) direction in OCT imaging. Therefore, the length of the glass spacer is designed to be 550 μm such that the beam divergence is slower with further beam waist position in lateral direction while the beam diverges faster with closer beam waist location in longitudinal direction.

For all the graphs of the beam profile in the present disclosure, the abscissa or x axis is the working distance measured perpendicularly from the optical axis Ox of the 1$^{st}$ and 2$^{nd}$ light guiding components and the ordinate or y axis is the beam radius defined as half of the 1/e$^2$ beam width.

Table 5 lists the beam parameters from the beam profile plots including beam divergence, beam waist location and beam waist size. The asterisk (*) in Table 5 indicates that the beam waist location is measured perpendicularly from the optical axis of the 1$^{st}$ and 2$^{nd}$ light guiding components.

TABLE 5

Beam parameters of the ball lens probe design according to the 5$^{th}$ embodiment

|  | Longitudinal direction | Lateral direction |
|---|---|---|
| Divergence angle @ 1310 nm | 0.06 rad | 0.012 rad |
| Divergence angle @ 633 nm | 0.03 rad | 0.007 rad |
| Beam waist location* @ 1310 nm | 0.92 mm | 1.65 mm |
| Beam waist location* @ 633 nm | 0.92 mm | 1.44 mm |
| Beam waist size radius @ 1310 nm | 18.4 μm | 38.1 μm |
| Beam waist size radius @ 633 nm | 5.5 μm | 18.2 μm |

[6th Embodiment] Specific Ball Lens Design: OD 300 μm Ball Lens with Glass Spacer Length in a Range of 500-800 μm This embodiment is similar to 5th embodiment with the same optical configuration for an optical probe having a ball lens of OD 300 μm, except that this embodiment specifies the range of length of the glass spacer (2nd light guiding component) that meets the specification listed in Table 2.

The range for the spacer length is between 500 μm to 800 μm while 550 μm is the preferred glass spacer length for a 300 μm OD ball lens.

Figure 7:
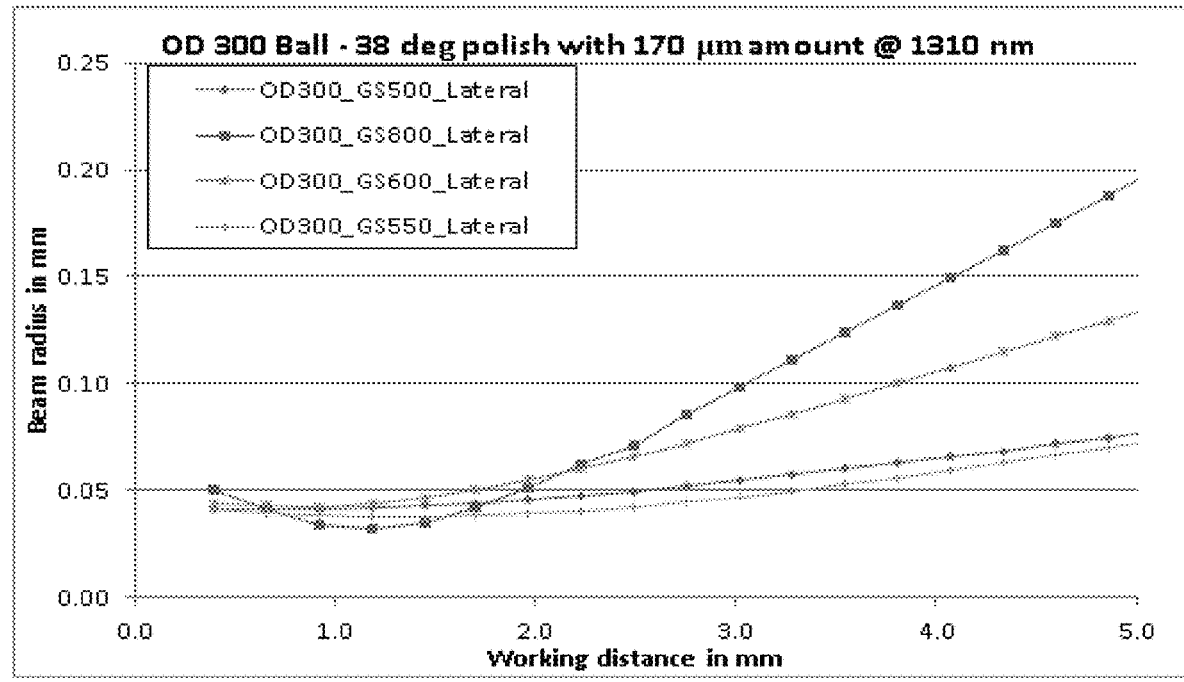
FIG. 7 is a plot showing a beam profile of a 300 μm OD ball lens (in contrast agent with sheath) with various glass spacer lengths in lateral direction. In all figures, OD and GS in the inset legend stand for outer diameter and glass spacer length, respectively.
Figure 8:
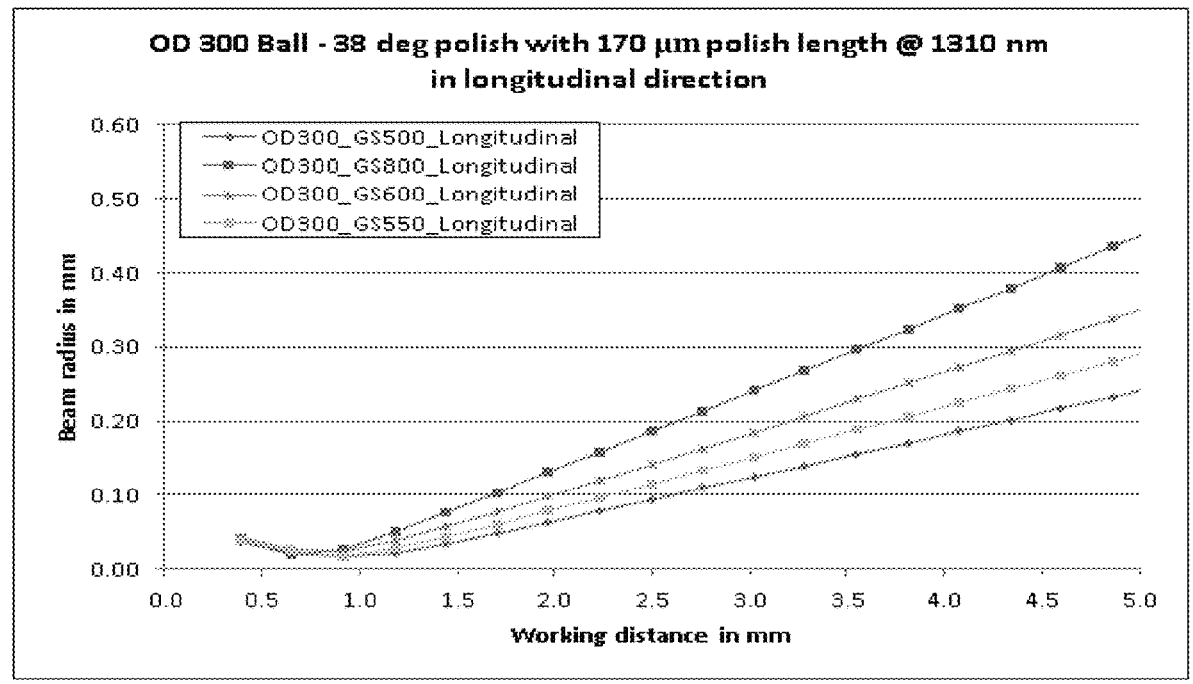
FIG. 8 is a plot showing a beam profile of a 300 μm OD ball lens (in contrast agent with sheath) with various glass spacer lengths in longitudinal direction.

FIG. 7 and FIG. 8 show the beam profile plots for the above designs that have the spacer lengths of 500 μm, 550 μm, 600 μm, and 800 μm at 1310 nm wavelength in lateral and longitudinal directions, respectively. The simulation was done by using Physical Wave Propagation model. The abscissa or x axis is the working distance measured perpendicularly from the optical axis of the 1st and 2nd light guiding components and the ordinate or y axis is the beam radius defined as half of the 1/e$^2$ beam width.

Table 6 lists the beam numerical parameters of an optical probe with OD 300 μm ball lens and the glass spacer length ranging from 500 μm to 800 μm that meet specifications listed in Table 2 from the beam profile plots. The parameters of the beam properties include beam divergence, beam waist location, and beam waist size.

Table 6 Beam parameters of the ball lens probe design according to the 6$^{th}$ embodiment. In Table 6, the beam waist location is measured perpendicularly from the optical axis of the 1st and 2nd light guiding components.

|  | Longitudinal direction | Lateral direction |
|---|---|---|
| Divergence angle @ 1310 nm | 0.059-0.105 rad | 0.011-0.0495 rad |
| Beam waist location@ 1310 nm | 0.65-0.92 mm | 0.95-1.7 mm |
| Beam waist size radius@ 1310 nm | 16.2-25 μm | 31.4-42.5 μm |

[7$^{th}$ Embodiment] Specific Ball Lens Design: OD 310 μm Ball Lens with Glass Spacer Length 630 μm In another embodiment, configuration parameters of an exemplary ball lens design are shown in Table 7.

TABLE 7

Ball lens probe configuration parameters

| Item | Material | Surface | Radius [mm] | Thickness [mm] |
|---|---|---|---|---|
| Light Source | — | 0 | Infinity | 0 |
| Glass spacer | Fused Silica | 1 | Infinity | 0.63 |
| Ball lens | Fused Silica | 2 | Infinity | 0 |
|  | Fused Silica | 3 | Infinity | 310 μm OD ball |
|  | Fused Silica | 4 | 0.155 | with 175 μm polishing length at 38 degrees |
| Inner medium | Air | 5 | Infinity | 0.137 |
| Sheath | Polymer | 6 | 0.292 | 0.101 |
|  |  | 7 | 0.393 |  |
| Outer medium | Contrast agent | 8 | Infinity | Working distance |
| Imaging plane | Tissue | 9 | Infinity | — |

The 7$^{th}$ embodiment is similar to the 5th embodiment except for the following listed parameters:

The ball lens has OD 310 μm and is angle polished with a polishing length 175 μm at 38 degrees, and the spacer length is 630 μm.

Figure 9:
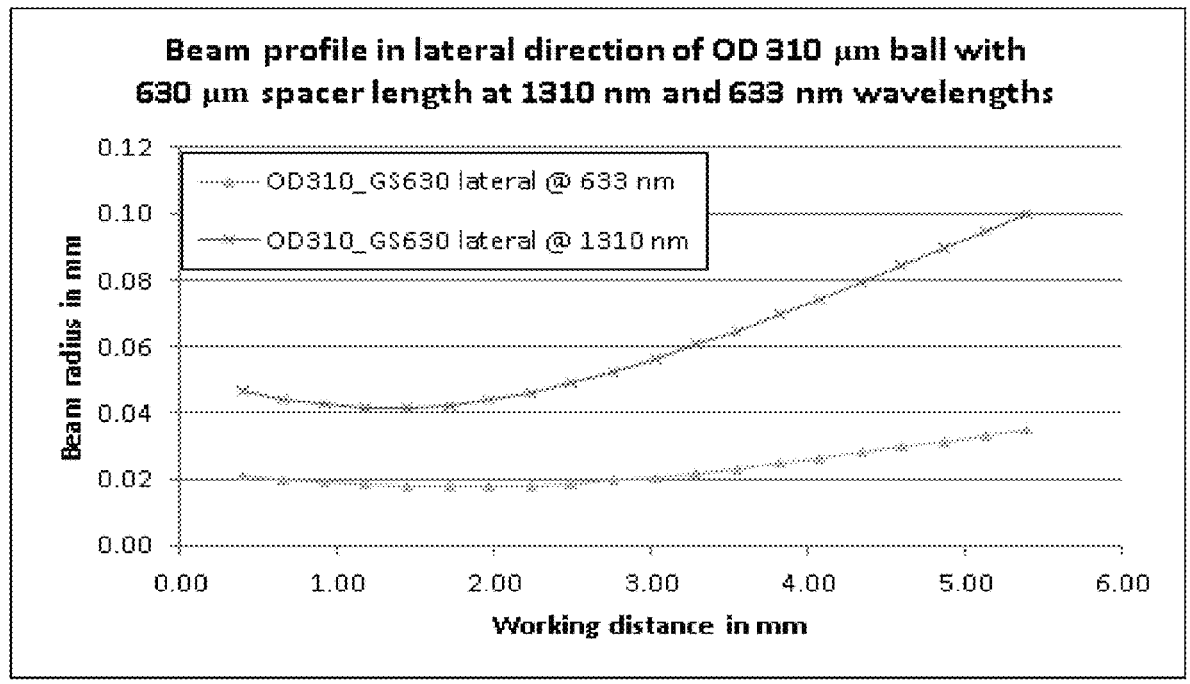
FIG. 9 is a graph showing a beam profile in lateral direction of a ball lens probe (in contrast agent with sheath) with 310 μm OD and 630 μm long glass spacer at 1310 nm and 633 nm wavelengths.
Figure 10:
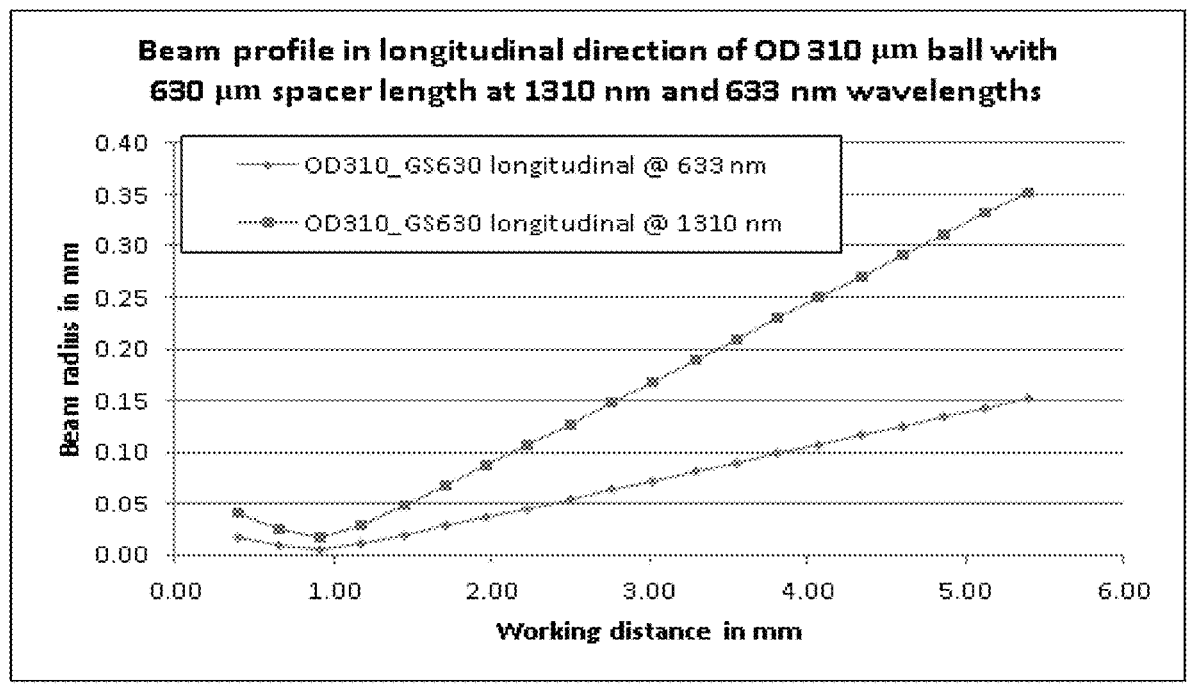
FIG. 10 shows a graph of a beam profile in longitudinal direction of a ball lens probe (in contrast agent with sheath) with 310 μm OD and 630 μm long glass spacer at 1310 nm and 633 nm wavelengths.

FIG. 9 and FIG. to show the beam profile plots for above design ball lens (7$^{th}$ embodiment) at 1310 nm and 633 nm wavelengths in lateral and longitudinal directions, respectively, where simulation was done using Physical Wave Propagation model. FIG. 9 and FIG. to demonstrate that the designed ball lens probe is substantially achromatic given that the beam waist locations between 1310 nm and 633 nm are within 0.3 mm difference. The x axis is the working distance measured perpendicularly from the optical axis of the 1st and 2nd light guiding components, and the y axis is the beam radius defined as half of the 1/e$^2$ beam width.

Table 8 lists the beam properties in numerical values of an optical probe with OD 310 μm ball lens and a 630 μm glass spacer length that meet specifications listed in Table 2. The parameters of the beam properties include beam divergence, beam waist location and beam waist size.

In this embodiment, optimization preference is given to the beam performance in lateral (scanning) direction due to much finer sampling rate in lateral direction than the one in longitudinal (pull-back) direction in OCT imaging. Therefore, the length of the glass spacer is designed to be 630 μm such that the beam divergence is slower with further beam waist position in lateral direction while the beam diverges faster with closer beam waist position in longitudinal direction.

TABLE 8

Beam parameters of the ball lens probe design

|  | Longitudinal direction | Lateral direction |
|---|---|---|
| Divergence angle @ 1310 nm | 0.078 rad | 0.019 rad |
| Divergence angle @ 633 nm | 0.034 rad | 0.007 rad |
| Beam waist location* @ 1310 nm | 0.92 mm | 1.71 mm |
| Beam waist location* @ 633 nm | 0.92 mm | 1.44 mm |
| Beam waist size radius @ 1310 nm | 18.0 μm | 41.6 μm |
| Beam waist size radius @ 633 nm | 5.3 μm | 17.7 μm |

[8th Embodiment] Specific Ball Lens Design: OD 310 μm Ball Lens with Glass Spacer Length 550-830 μm This embodiment is similar to 7th embodiment with the same optical configuration for an OD 310 μm ball lens probe except that this embodiment specifies the range of length of the glass spacer (2nd light guiding component) that meets the specification listed in Table 2.

The range for the spacer length is between 550 μm to 830 μm while 630 μm is the preferred glass spacer length for a 310 μm OD ball lens.

FIG. 11 and FIG. 12 show the beam profile plots for the above ball lens design that have the spacer lengths of 550 μm, 610 μm, 630 μm, 650 μm, 700 μm, 800 μm and 830 μm at 1310 nm wavelength in lateral and longitudinal directions simulated using Physical Wave Propagation model, respectively. The abscissa or x axis is the working distance measured perpendicularly from the optical axis of the 1st and 2nd light guiding components and the ordinate or y axis is the beam radius defined as half of the $1/e^2$ beam width.

Table 9 lists the beam properties in numerical values of an optical probe with OD 310 μm ball lens and a spacer length ranging from 550 μm to 830 μm that meet specifications listed in Table 2 from the beam profile plots. The parameters of the beam properties include beam divergence, beam waist location and beam waist size.

TABLE 9

Beam parameters of the ball lens probe design according tot the 8th embodiment

| | Longitudinal direction | Lateral direction |
|---|---|---|
| Divergence angle @ 1310 nm | 0.066-0.11 rad | 0.016-0.048 rad |
| Beam waist location @ 1310 nm | 0.65-0.92 mm | 0.95-1.71 mm |
| Beam waist size radius @ 1310 nm | 18.0-23.0 μm | 35.1-49.0 μm |

[9th Embodiment] Specific Ball Lens Design: OD 320 μm Ball Lens with Glass Spacer Length 650 μm In another embodiment, an exemplary ball lens design configuration parameters is shown in Table 10.

TABLE 10

Ball lens probe configuration parameters

| Item | Material | Surface | Radius [mm] | Thickness [mm] |
|---|---|---|---|---|
| Light Source | — | 0 | Infinity | 0 |
| Glass spacer | Fused Silica | 1 | Infinity | 0.65 |
| Ball lens | Fused Silica | 2 | Infinity | 0 |
| | Fused Silica | 3 | Infinity | 320 μm OD ball |
| | Fused Silica | 4 | 0.16 | with 180 μm polishing length at 38 degrees |
| Inner medium | Air | 5 | Infinity | 0.132 |
| Sheath | POLYMER | 6 | 0.292 | 0.101 |
| | | 7 | 0.393 | |
| Outer medium | Contrast agent | 8 | Infinity | 2 |
| Imaging plane | Tissue | 9 | Infinity | — |

The ninth embodiment is similar to the 5th and 7th embodiments except for the following listed parameters:

The ball lens has OD 320 μm and is angle polished with a polishing length 180 μm at 38 degrees, and the spacer length is 650 μm. In this embodiment, the incident angle of the chief ray to the inner surface of the sheath is about 19.2 degrees.

Figure 13:
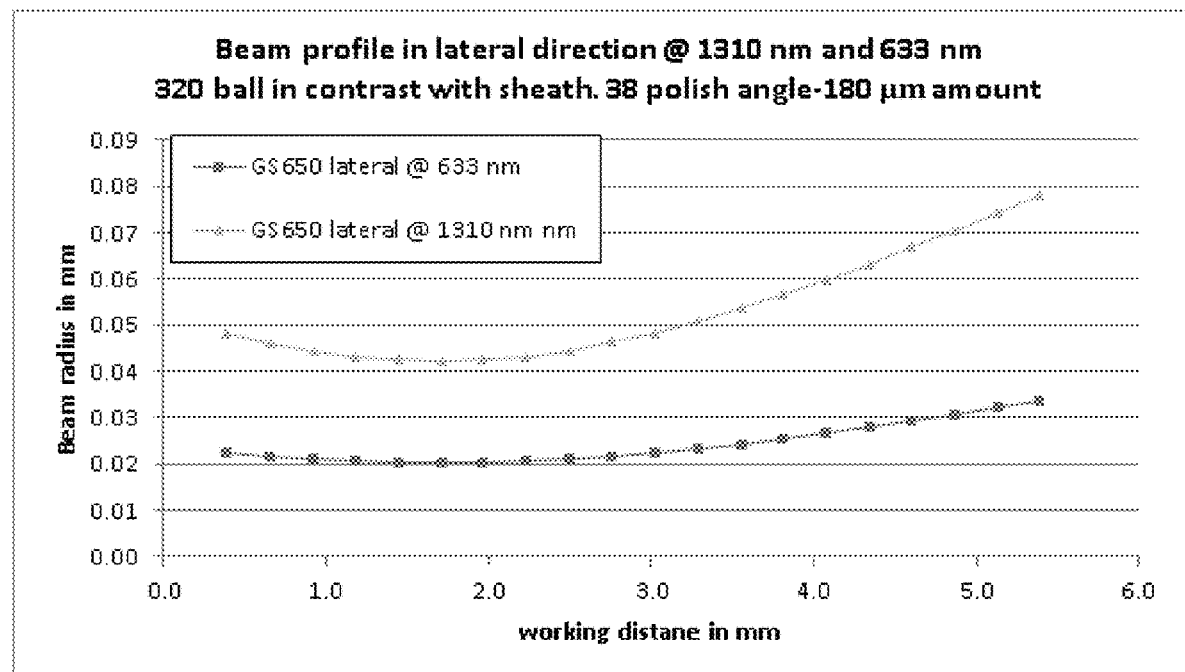
FIG. 13 is a graph showing a beam profile in lateral direction of a ball lens probe (in contrast agent with sheath) with 320 μm OD and 650 μm long glass spacer at 1310 nm and 633 nm wavelengths.
Figure 14:
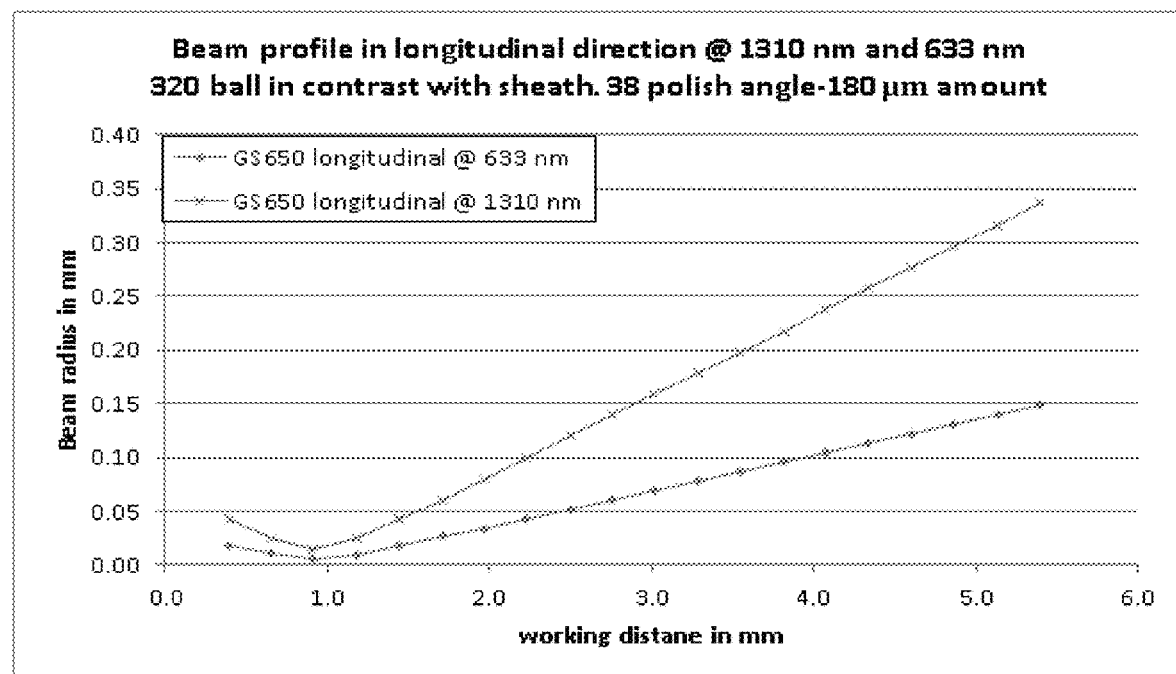
FIG. 14 is a graph showing a beam profile in longitudinal direction of a ball lens probe (in contrast agent with sheath) with 320 μm OD and 650 μm long glass spacer at 1310 nm and 633 nm wavelengths.

FIG. 13 and FIG. 14 show beam profile plots for the above design at 1310 nm and 633 nm wavelengths in lateral and longitudinal directions, respectively, simulated using Physical Wave Propagation model. FIG. 13 and FIG. 14 demonstrate that the ball lens probe design is substantially achromatic given that the beam waist locations between 1310 nm and 633 nm are within 0.3 mm difference. The x axis is the working distance measured perpendicularly from the optical axis of the 1st and 2nd light guiding components and the y axis is the beam radius defined as half of the $1/e^2$ beam width.

Table 11 lists the beam profile properties of an optical probe with OD 320 μm ball lens and a 650 μm glass spacer length that meet specifications listed in Table 2. The parameters of the beam properties include beam divergence, beam waist location and beam waist size. Beam waist location is measured perpendicularly from the optical axis of the 1st and 2nd light guiding components.

TABLE 11

Beam parameters of the ball lens probe design

| | Longitudinal direction | Lateral direction |
|---|---|---|
| Divergence angle @ 1310 nm | 0.075 rad | 0.0145 rad |
| Divergence angle @ 633 nm | 0.033 rad | 0.0056 rad |
| Beam waist location* @ 1310 nm | 0.92 mm | 1.71 mm |
| Beam waist location* @ 633 nm | 0.92 mm | 1.71 mm |
| Beam waist size radius @ 1310 nm | 20.2 μm | 42.3 μm |
| Beam waist size radius @ 633 nm | 5.3 μm | 15.3 μm |

*Beam waist location is measured perpendicularly away from optical axis of 1st and 2nd light guiding components.

[10th Embodiment] Specific Ball Lens Design: OD 320 μm Ball Lens with Glass Spacer Length 570 μm-850 μm The tenth embodiment is similar to the 9th embodiment with the same optical configuration for an OD 320 μm ball lens probe except that this embodiment specifies a range of lengths for the glass spacer (2nd light guiding component) that meets the specification listed in Table 2. The range for the spacer length is between 570 μm to 850 μm, while 650 μm is the preferred glass spacer length for a 320 μm OD ball lens.

Figure 15:
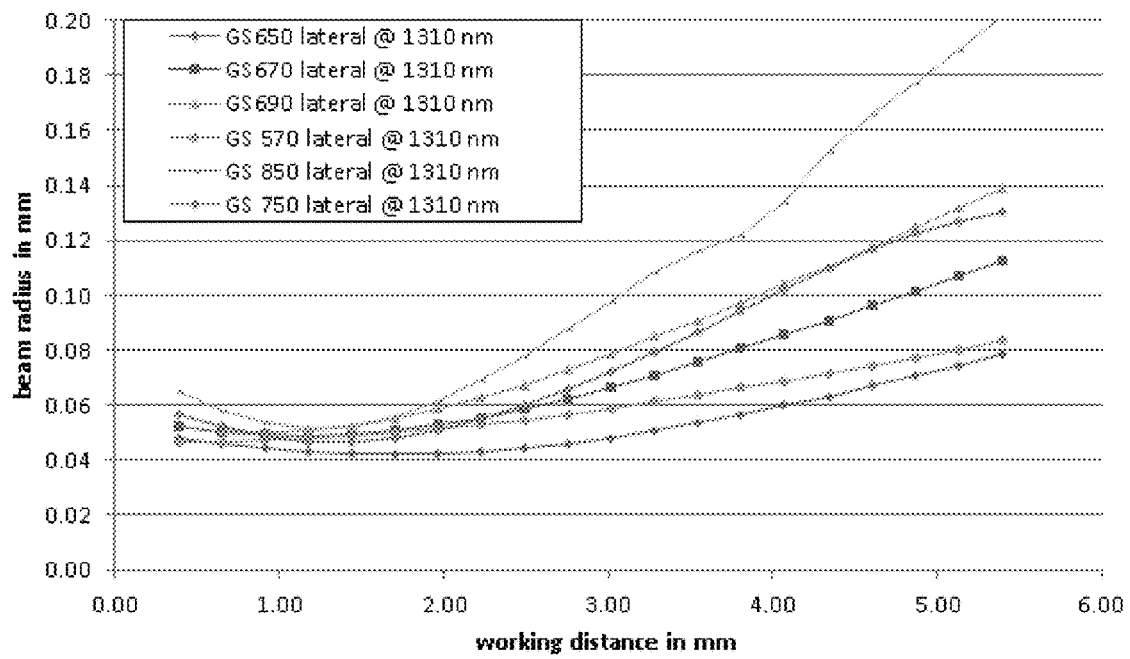
FIG. 15 is a graph showing a beam profile of a 320 μm OD ball lens (in contrast agent with sheath) with various glass spacer lengths in lateral direction.
Figure 16:
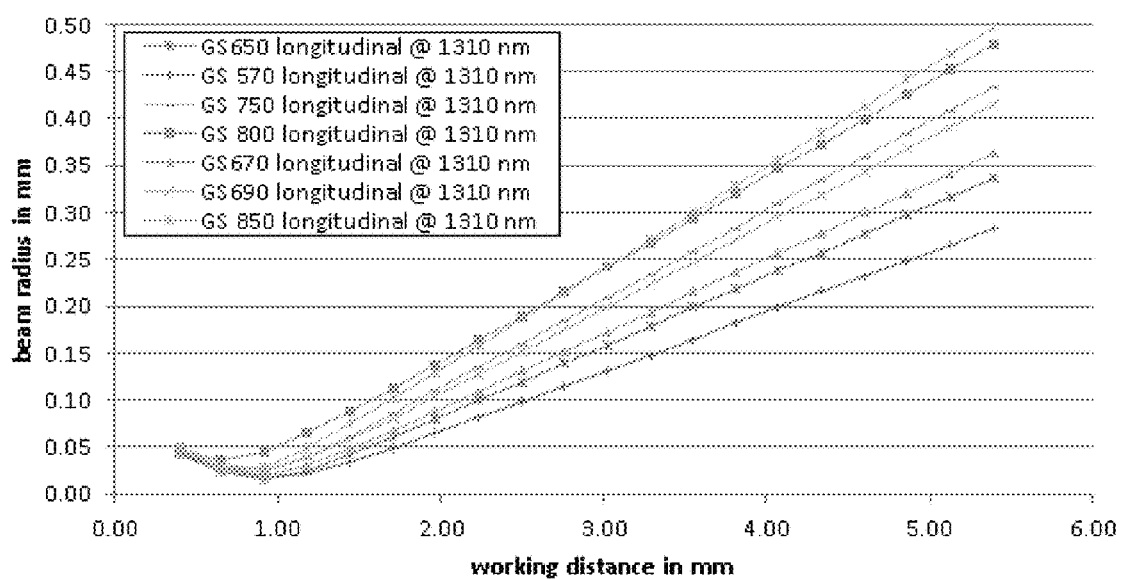
FIG. 16 is a graph showing a beam profile of a 320 μm OD ball lens (in contrast agent with sheath) with various glass spacer lengths in longitudinal direction.

FIG. 15 and FIG. 16 show the beam profile plots for the above optical probe designs that have the spacer lengths of 570 μm, 650 μm, 670 μm, 690 μm, 750 μm and 850 μm at 1310 nm wavelength in lateral and longitudinal directions, respectively, simulated using Physical Wave Propagation model. In the plots, the x axis is the working distance measured perpendicularly from the optical axis of the 1st and 2nd light guiding components and the y axis is the beam radius defined as half of the $1/e^2$ beam width.

Table 12 lists the beam properties of the optical probe with OD 320 μm ball lens and a spacer length ranging from 570 μm to 850 μm that meet specifications listed in Table 2 from the beam profile plots. The parameters of the beam properties include beam divergence, beam waist location and beam waist size.

TABLE 12

Beam parameters of the ball lens probe design

| | Longitudinal direction | Lateral direction |
|---|---|---|
| Divergence angle @ 1310 nm | 0.064-0.11 rad | 0.011-0.050 rad |
| Beam waist location @ 1310 nm | 0.65-0.92 mm | 0.91-1.97 mm |
| Beam waist size radius @ 1310 nm | 18.0-28.0 μm | 42.4-51.4 μm |

[11th Embodiment] Specific Ball Lens Design: OD 330 μm Ball Lens with Glass Spacer Length 800 μm In another embodiment, an exemplary ball lens design configuration parameters is shown in Table 13.

TABLE 13

Ball lens probe configuration parameters

| Item | Material | Surface | Radius [mm] | Thickness [mm] |
|---|---|---|---|---|
| Light Source | — | 0 | Infinity | 0 |
| Glass spacer rod | Fused Silica | 1 | Infinity | 0.80 |
| Ball lens | Fused Silica | 2 | Infinity | 0 |
| | Fused Silica | 3 | Infinity | 330 μm OD ball |
| | Fused Silica | 4 | 0.165 | with 185 μm polishing length at 38 degrees |
| Inner medium | Air | 5 | Infinity | 0.127 |
| Sheath | Polymer | 6 | 0.292 | 0.101 |
| | | 7 | 0.393 | |
| Outer medium | Contrast agent | 8 | Infinity | Working distance |
| Imaging plane | Tissue | 9 | Infinity | — |

This 11th embodiment is similar to the 5th, 7th and 9th embodiments except for the following listed parameters:

The spacer length is 800 μm; and the ball lens has OD 330 μm and is angle polished with a polishing length of 185 μm at 38 degrees. In this embodiment, the incident angle of the chief ray in longitudinal direction to the inner surface of the sheath is about 19.1 degrees.

Figure 17:
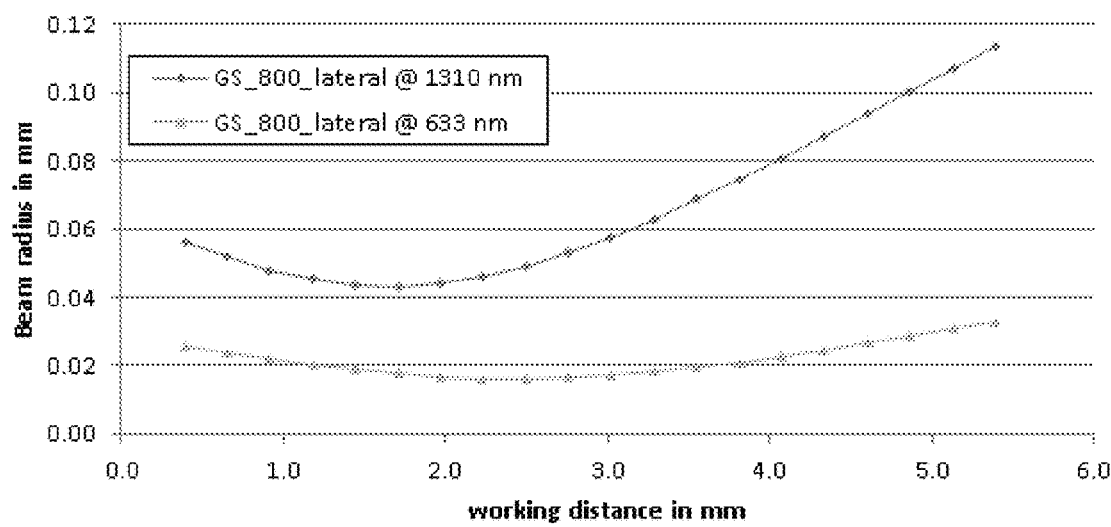
FIG. 17 is a graph showing a beam profile in lateral direction of a ball lens probe (in contrast agent with sheath) with 330 μm OD and 800 μm long glass spacer at 1310 nm and 633 nm wavelengths.
Figure 18:
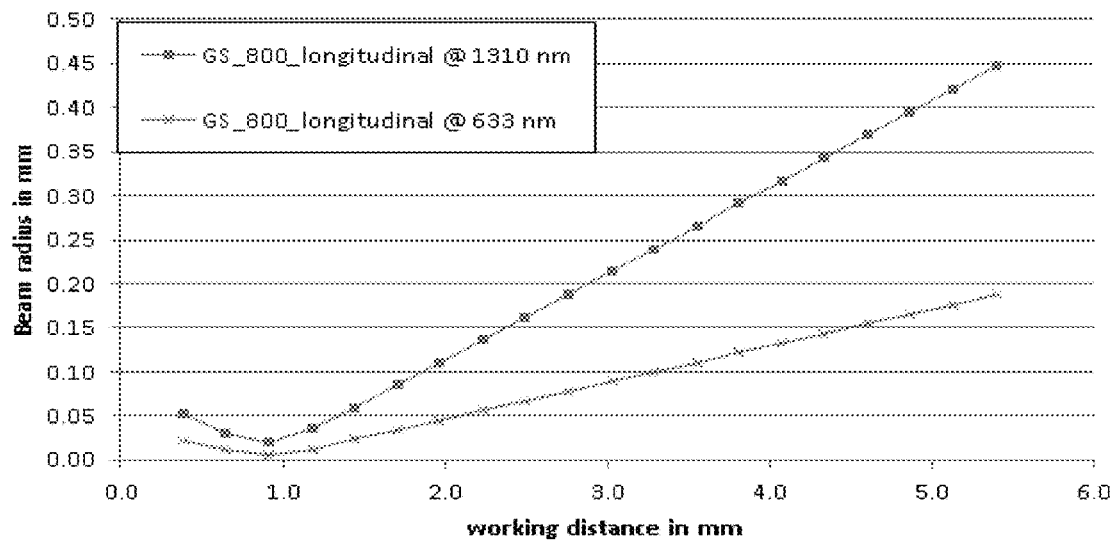
FIG. 18 is a graph showing a beam profile in longitudinal direction of a ball lens probe (in contrast agent with sheath) with 330 μm OD and 800 μm long glass spacer at 1310 nm and 633 nm wavelengths.

FIG. 17 and FIG. 18 show the beam profile plots of above design at 1310 nm and 633 nm wavelengths in lateral and longitudinal directions, respectively, simulated by Physical Optics Wave Propagation. The abscissa or x axis is the working distance measured perpendicularly from the optical axis of the $1^{st}$ and $2^{nd}$ light guiding components and the ordinate or y axis is the beam radius defined as half of the $1/e^2$ beam width.

Table 14 tabulates the beam properties of an optical probe with OD 330 μm ball lens and an 800 μm glass spacer length that meet the specifications listed in Table 2. The parameters of the beam properties include beam divergence, beam waist location and beam waist size. Beam waist location is measured perpendicularly from the optical axis of the $1^{st}$ and $2^{nd}$ light guiding components.

TABLE 14

Beam parameters of the ball lens probe design according to the 11th embodiment

| | Longitudinal direction | Lateral direction |
|---|---|---|
| Divergence angle @ 1310 nm | 0.099 rad | 0.025 rad |
| Divergence angle @ 633 nm | 0.042 rad | 0.008 rad |

TABLE 14-continued

Beam parameters of the ball lens probe design according to the 11th embodiment

| | Longitudinal direction | Lateral direction |
|---|---|---|
| Beam waist location* @ 1310 nm | 0.92 mm | 1.71 mm |
| Beam waist location* @ 633 nm | 0.92 mm | 2.50 mm |
| Beam waist size radius @ 1310 nm | 20.5 μm | 42.8 μm |
| Beam waist size radius @ 633 nm | 5.1 μm | 16.2 μm |

[12th Embodiment] Specific Ball Lens Design: OD 330 μm Ball Lens with Glass Spacer Length 600-1000 μm The 12th embodiment is similar to the 11th embodiment with the same optical configuration for an OD 330 μm ball lens probe except that this embodiment specifies a range of lengths of the glass spacer ($2^{nd}$ light guiding component) that meets the specification listed in Table 2. The range for the spacer length is between 600 μm to 1000 μm while 800 μm is the preferred glass spacer length for a 330 μm OD ball lens.

Figure 19:
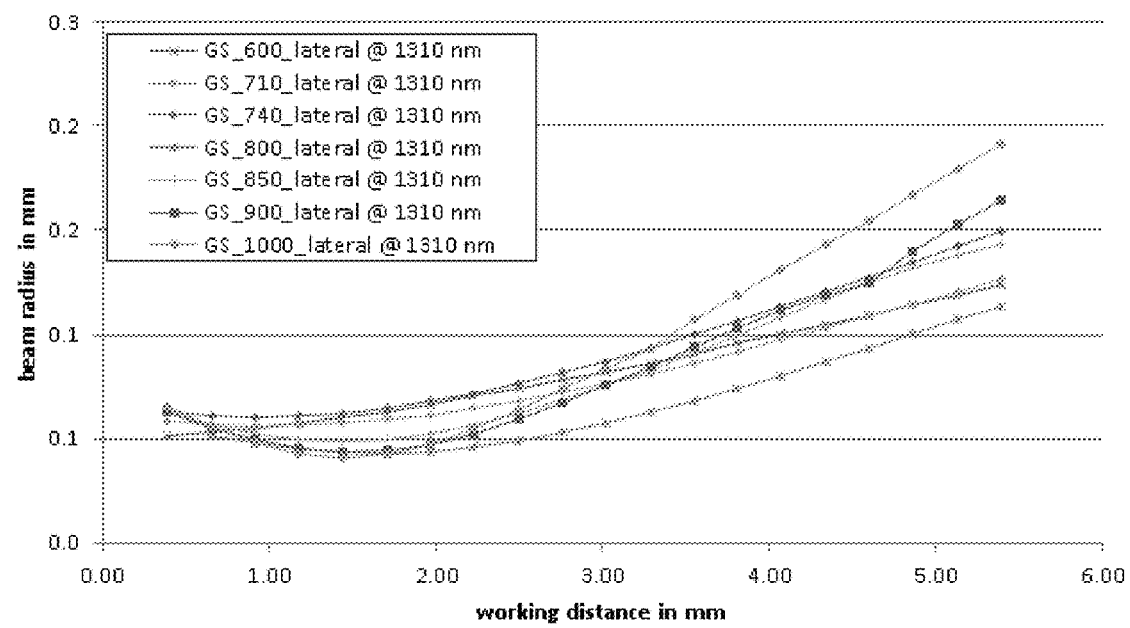
FIG. 19 is graph showing the beam profile of a 330 μm OD ball lens with spacer lengths of 600, 710, 740, 800, 850, 900, and 1000 μm (in contrast agent with sheath) at 1310 nm wavelength in lateral direction simulated by Physical Optics Wave Propagation Model.
Figure 20:
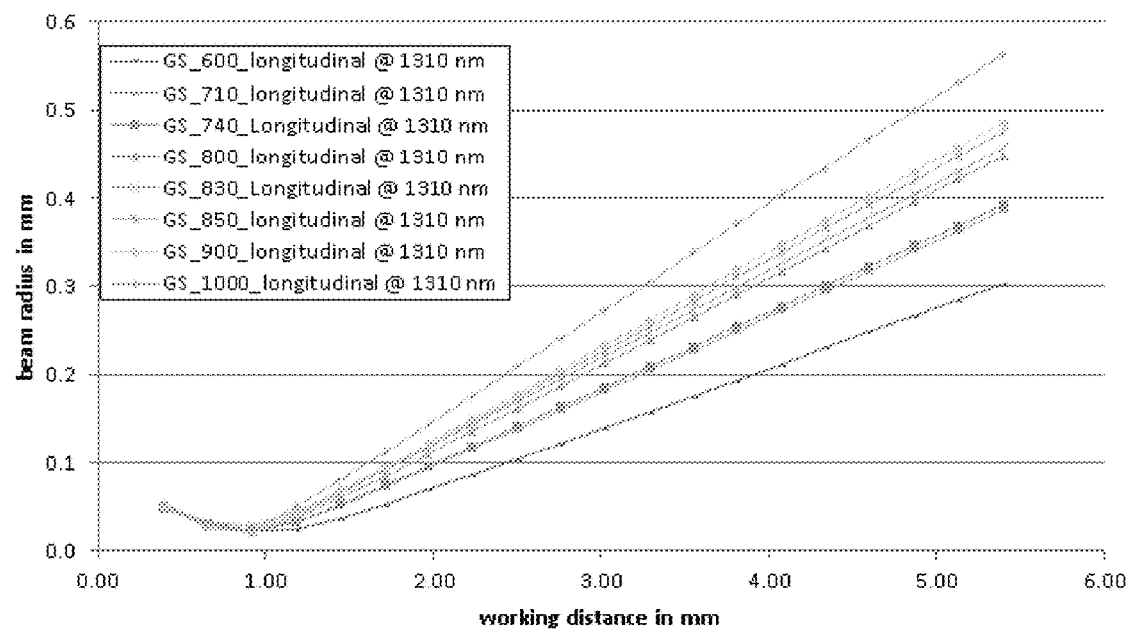
FIG. 20 is graph showing the beam profile of a 330 μm OD ball lens with spacer lengths of 600, 710, 740, 800, 850, 900, and 1000 μm (in contrast agent with sheath) at 1310 nm wavelength in longitudinal direction simulated by Physical Optics Wave Propagation Model.

FIG. 19 and FIG. 20 show the beam profile plots for the above optical probe designs that have the spacer lengths of 60 μm, 710 μm, 740 μm, 800 μm, 850 μm, 900 μm, and 1000 μm at 1310 nm wavelength in lateral and longitudinal directions, respectively, simulated by Physical Optics Wave Propagation Model. The x axis is the working distance measured perpendicularly from the optical axis of the $1^{st}$ and $2^{nd}$ light guiding components and the y axis is the beam radius defined as half of the $1/e^2$ beam width.

Table 15 lists the beam properties of an optical probe with OD 330 μm ball lens and a spacer length ranging from 600 μm to 1000 μm that meet specifications listed in Table 2 from the beam profile plots. The parameters of the beam properties include beam divergence, beam waist location, and beam waist size.

TABLE 15

Beam parameters of the ball lens probe design according to the 12 embodiment

| | Longitudinal direction | Lateral direction |
|---|---|---|
| Divergence angle @ 1310 nm | 0.0687-0.12 rad | 0.015-0.046 rad |
| Beam waist location @ 1310 nm | 0.92 mm | 0.91-1.97 mm |
| Beam waist size radius @ 1310 nm | 20.5-28.2 μm | 40.7-60.6 μm |

[13th Embodiment] Specific Ball Lens Design: OD 340 μm Ball Lens with Glass Spacer Length 850 μm In another embodiment, an exemplary ball lens design configuration parameters is shown in Table 16.

TABLE 16

Ball lens probe configuration parameters according to the 13$^{th}$ embodiment

| Item | Material | Surface | Radius [mm] | Thickness [mm] |
|---|---|---|---|---|
| Light Source | — | 0 | Infinity | 0 |
| Glass spacer rod | Fused Silica | 1 | Infinity | 0.85 |
| Ball lens | Fused Silica | 2 | Infinity | 0 |
|  | Fused Silica | 3 | Infinity | 340 µm OD ball with 185 µm polishing length at 38 degrees |
|  | Fused Silica | 4 | 0.17 |  |
| Inner medium | Air | 5 | Infinity | 0.113 |
| Sheath | polymer | 6 | 0.292 | 0.101 |
|  |  | 7 | 0.393 |  |
| Outer medium | Contrast agent | 8 | Infinity | Working distance |
| Imaging plane | Tissue | 9 | Infinity | — |

The 13$^{th}$ embodiment is structurally similar to the 5$^{th}$, 7$^{th}$, 9$^{th}$, 11$^{th}$ embodiments except for the following listed parameters:

The spacer length is 850 µm. The ball lens has OD 340 µm and is angle polished with a polishing length 190 µm at 38 degrees. According to this embodiment, the incident angle of the chief ray in longitudinal direction to the inner surface of the sheath is about 19.0 degrees.

Figure 21:
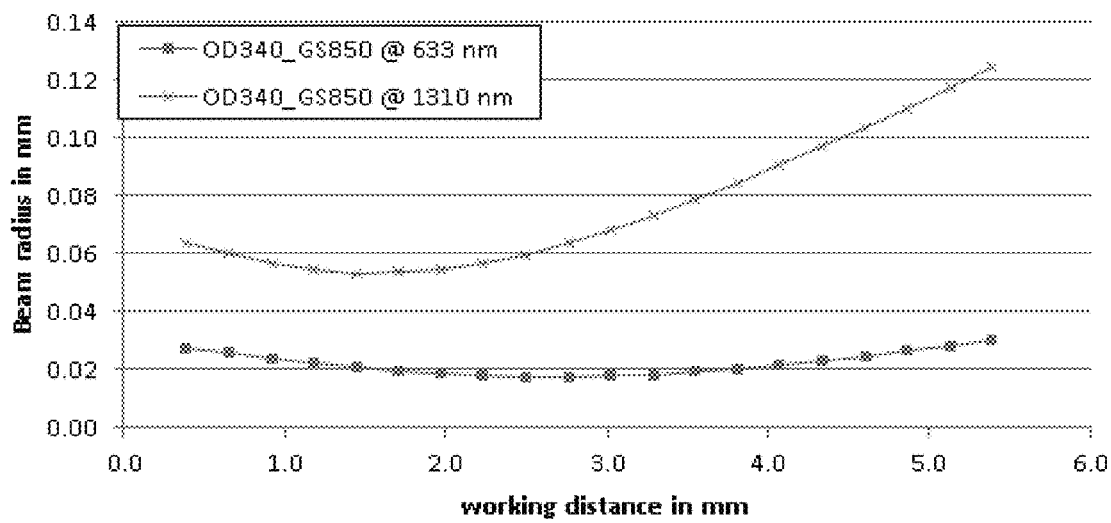
FIG. 21 is a graph showing a beam profile in lateral direction of a ball lens probe (in contrast agent with sheath) with 340 μm OD and 850 μm long glass spacer at 1310 nm and 633 nm wavelengths.
Figure 22:
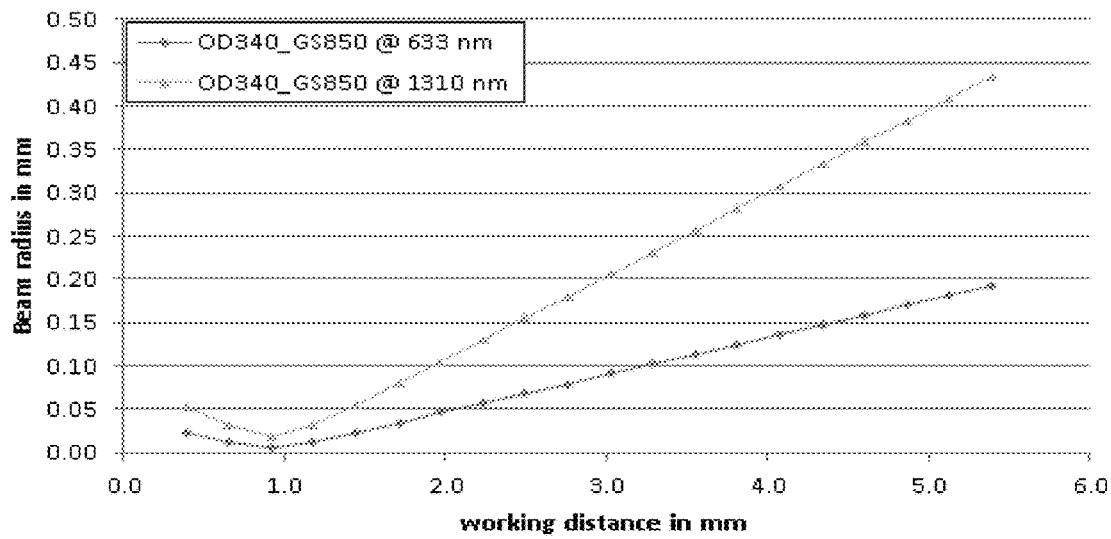
FIG. 22 is a graph showing a beam profile in longitudinal direction of a ball lens probe (in contrast agent with sheath) with 340 μm OD and 850 μm long glass spacer at 1310 nm and 633 nm wavelengths.

FIG. 21 and FIG. 22 show the beam profile plots for the above optical probe design at 1310 nm and 633 nm wavelengths in lateral and longitudinal directions, respectively. The beam profiles were modeled using the parameters listed in Table 16 with Physical Wave Propagation model. The x axis is the working distance measured perpendicularly from the optical axis of the 1$^{st}$ and 2$^{nd}$ light guiding components and the y axis is the beam radius defined as half of the 1/e$^2$ beam width.

Table 17 lists the beam properties of an optical probe with OD 340 µm ball lens and an 850 µm glass spacer length that meet the specifications listed in Table 2. The parameters of the beam properties include beam divergence, beam waist location and beam waist size. The beam waist location is measured perpendicularly from the optical axis of the 1st and 2nd light guiding components lens.

TABLE 17

Beam parameters of the ball lens probe design according to the 13$^{th}$ embodiment

|  | Longitudinal direction | Lateral direction |
|---|---|---|
| Divergence angle @ 1310 nm | 0.097 rad | 0.026 rad |
| Divergence angle @ 633 nm | 0.043 rad | 0.007 rad |
| Beam waist location* @ 1310 nm | 0.92 mm | 1.44 mm |
| Beam waist location* @ 633 nm | 0.92 mm | 2.76 mm |
| Beam waist size radius @ 1310 nm | 19.1 µm | 53.2 µm |
| Beam waist size radius @ 633 nm | 5.0 µm | 17.6 µm |

[14th Embodiment] Specific Ball Lens Design: OD 340 µm Ball Lens with Glass Spacer Length 750-1050 µm This embodiment is similar to 13th embodiment with the same optical configuration for an OD 340 µm ball lens probe except that this embodiment specifies the range of length of the glass spacer (2nd light guiding component) that meets the specification listed in Table 2. The range for the spacer length is between 750 µm to 1050 µm while 850 µm is the preferred glass spacer length for a 340 µm OD ball lens.

Figure 23:
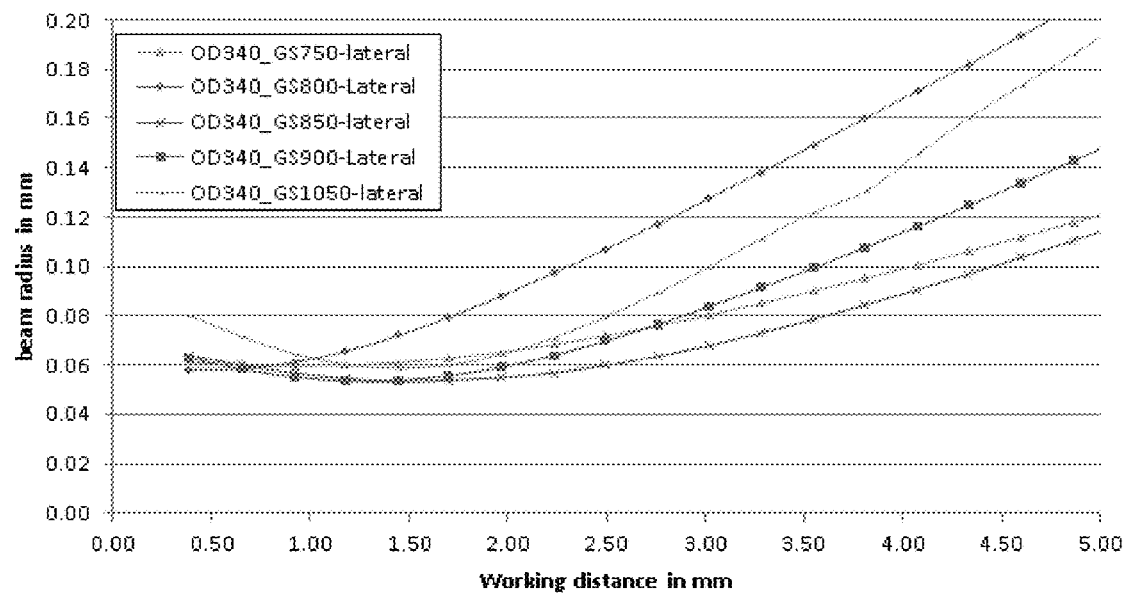
FIG. 23 is a graph showing a beam profile of a 340 μm OD ball lens (in contrast agent with sheath) with various glass spacer lengths in lateral direction.
Figure 24:
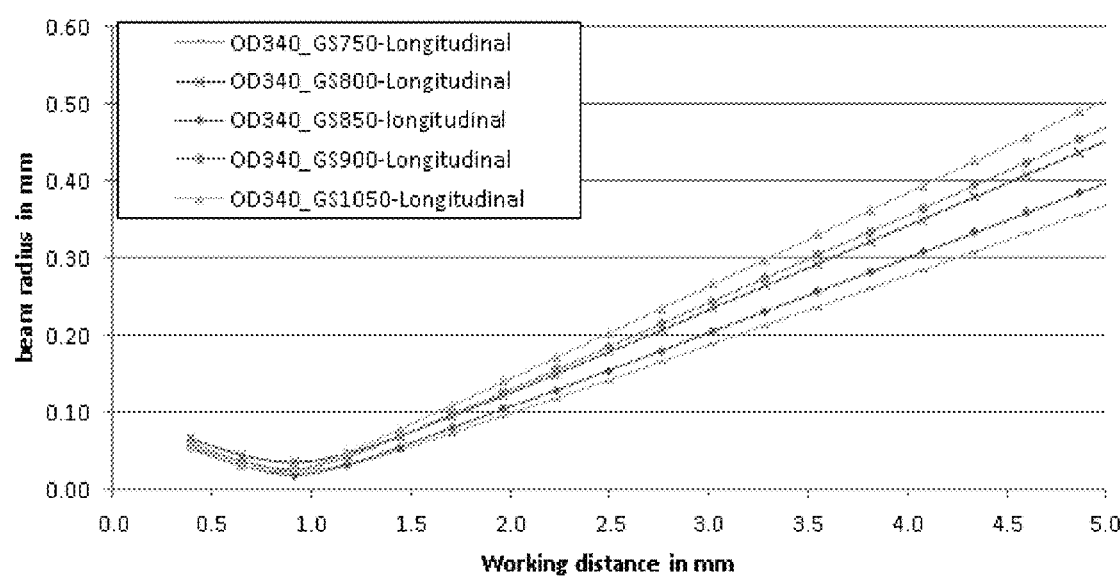
FIG. 24 is a graph showing a beam profile of a 340 μm OD ball lens (in contrast agent with sheath) with various glass spacer lengths in longitudinal direction.

FIG. 23 and FIG. 24 show the beam profile plots for the above optical probe designs that have the spacer lengths of 750 µm, 800 µm, 850 µm, 900 µm, and 1050 µm at 1310 nm wavelength in lateral and longitudinal directions, respectively, simulated by Physical Optics Wave Propagation Model.

Table 18 lists the beam properties of an optical probe with OD 340 µm ball lens and a spacer length ranging from 750 µm to 1050 µm that meet specifications listed in Table 2 from the beam profile plots. The parameters of the beam properties include beam divergence, beam waist location, and beam waist size. Similar to other embodiments, in Table 18, the beam waist location is measured perpendicularly from the optical axis of the 1st and 2nd light guiding components.

TABLE 18

Beam parameters of the ball lens probe design for OD 340 µm ball lens

|  | Longitudinal direction | Lateral direction |
|---|---|---|
| Divergence angle @ 1310 nm | 0.09-0.12 rad | 0.026-0.043 rad |
| Beam waist location @ 1310 nm | 0.92 mm | 0.4-1.71 mm |
| Beam waist size radius @ 1310 nm | 19-25.2 µm | 53.7-61.0 µm |

[15$^{th}$ Embodiment] Design Method for Determining the Range of Acceptable Glass Spacer Length for a Specific Ball Lens Diameter In a design process, given the fixed parameters listed in Table 3 both ball lens diameter and glass spacer length are the main parameters that control the beam properties. For different ball lens diameters there are corresponding glass spacer lengths that could result in similar beam profile performance such as beam waist location and far field divergence angle. This section of the disclosure explains the relation between the ball lens diameter and the glass spacer length in which similar beam characteristics can be achieved in different design configurations.

[Mathematical Model]

The propagation of a spherical focusing beam from a coherent light source focused by a lens can be approximated and simplified by using a lens formula of geometrical optics and introducing an additional parameter, the Rayleigh range of a Gaussian beam. See, for example, "Focusing of spherical Gaussian Beams" by Sidney A. Self, 1983. The lens formula for a Gaussian beam is expressed in Equation 1:

$$1 \Big/ \left( s + \frac{Z_R^2}{(s-f)} \right)^{+1/s'=1/f} \quad \text{(Equation 1)}$$

Where s is the object distance, s' is the image distance, $Z_R$ is Rayleigh range and f is the focal length of the lens.

Since such model has assumptions and simplifications, the numerical results of beam properties are not absolutely accurate, but nevertheless it is useful to predict the trend of beam behavior in the initial design process. The following example of the design approach is given in terms of a ball lens configuration listed in Table 3 and the exemplary plots (FIG. 25 and FIG. 26) are only in lateral direction. However, with the appropriate approximation and calculation in s, $Z_R$ and f, the results apply equally well for other optical configuration such as GRIN lens probe and/or with different sheath dimensions.

[Approximation and Derivation of Ball Lens Design Parameters Relationship]

In Equation 1, the object distance "s" is regarded as the beam waist position of the input beam, which is at the output of the 1st light guiding component (i.e. at the distal end of the double clad fiber). Therefore, "s" can be approximated to be the optical length of the distal ball lens probe expressed in Equation 2:

$$s \sim n \times \text{total length} \qquad \text{(Equation 2)}$$

Where total length=glass spacer length+ball lens diameter and n is the refractive index of the glass spacer. See FIG. 2B.

The image distance s' in Equation 1 is regarded as the beam waist position of the output beam. The relation between the optical probe total length vs. the beam waist location in lateral direction of the output beam with different ball lens diameters is illustrated in FIG. 25 based on Equation 1 and Equation 2. From FIG. 25, one can observe that the curves of different ball lens diameter shift from each other towards the right. This shift indicates that if the curves can be shifted to the left to be overlapped with each other, similar characteristics of the output beam (i.e., nearly the same beam waist position in y axis) from different diameters of the ball lens probes can be achieved.

[Method of Determining the Initial Ball Lens Design Parameters]

The ball lens diameter and/or glass spacer length can be designed using the "ratio x" of the optical probe total length to ball lens diameter squared. Specifically, based on the above observations of the behavior of Gaussian beams and the shifting of the curves for different ball lens diameters shown in FIG. 25, the present disclosure proposes to utilize a "ratio x" with a defined numerical range to derive the proper spacer length for a given ball lens diameter, and to reach the desired performance within the desired specification. The numerical range of the ratio x is determined by the acceptable range of beam properties (for example, the acceptable beam waist location in lateral direction ranges from 1-1.5 mm).

FIG. 26 shows a modification of the curves plotted in FIG. 25. The area 2600 marked by a dashed line in FIG. 26 represents the area where the beam performance falls into the design specifications listed in Table 2. Notably, this area corresponds to a numerical range of ratio x between 8.3 and 12.3 [1/mm] (in the case where the length unit in equation 3 is in mm), and the beam waist location in lateral direction is roughly between 1 and 1.5 mm. Notice that x can be applied to any arbitrary function y as function of x, and the numerical range will be changed as y(x) accordingly. For example, if $y(x)=x^2+1$, the numerical range would become 69.89-152.29 for a given ball lens diameter to find the length range of the glass spacer. In addition, if the length unit is changed from mm to µm or other units, the numerical value of ratio x will be scaled accordingly. For example, if the length unit in Equation 3 is in µm, ratio x is scaled to be in the range from $8.3 \times 10^3$ to $12.3 \times 10^{-3}$ [1/µm].

The change of effective focal length of different ball lens optical probes in a catheter (including a sheath having fixed optical power) can be approximated to be linearly proportional to the change of the ball lens diameter. FIG. 26 illustrates that by plotting the relation between beam waist location in lateral direction and the ratio x, which is expressed in Equation 3, the curves on the positive falling wings of the plots overlap each other. The overlap region indicates that the beam properties (e.g., the beam waist location in lateral direction as shown in y axis of the graph) of different diameter ball lens probes at a given value of ratio x in the overlap region would be almost the same.

$$x = (\text{Glass spacer length} + \text{ball diameter})/\text{ball dimeter}^2 \qquad \text{(Equation 3)}$$

This technique is useful in the initial design phase and the steps are described in the following section. Process for designing ball lens optical probe optimized for balanced astigmatism and substantially achromatic performance between 633±10 nm and 1310 nm:

Step 1: Simulate the relation between beam performance parameter (e.g., beam waist location) vs. design parameters (e.g., ball lens diameter and glass spacer length) with the design parameters for different ball lens diameters and/or different refractive index of the ball lens. If using GRIN lens, simulate for different GRIN lens length.

Step 2: Adjust x axis by taking the design parameters in ratio ("ratio x" in Equation 3) such that the curves for different ball lens diameter, different refractive indices of the ball lens, or if using GRIN lens, for different GRIN lens length overlap.

Step 3: The simulation of step 1 and step 2 could be based on Equation 1, or other similar Gaussian beam propagation models such as ABCD matrix with Gaussian Beam properties. See. for example, P. A. Bélanger, "Beam propagation and the ABCD ray matrices", Opt. Lett. 16 (4), 196 (1991) and A. E. Siegman, Lasers, University Science Books, Mill Valley, Calif. (1986)]. In particular, simulate beam waist location in lateral direction vs. total length/(ball lens diameter)^2 for different ball lens diameters as shown in FIG. 26.

Step 4: Find the overlap range of curves of different ball lens diameters in the x axis that satisfies the performance specifications in y axis of FIG. 26.

Step 5: For a certain ball lens diameter (or in general certain optical power of the distal optics), one can derive the range of length for glass spacer based on the given range in x axis, and the optics configuration (ball lens diameter and glass spacer length) within such range should result in beam performance close or within specifications.

Step 6: Use the above range to fine tune the design to achieve the best performance.

Examples of using the above design technique to achieve desirable performance of different ball lens diameters can be seen from previous embodiments (5th-14th). Table 19 summarizes the range of ratio x for different ball lens diameters and the corresponding range of glass spacer length from 6th, 8th, 10th, 12th, and 14th embodiments.

One can see that the ranges of ratio x of 5th-14th embodiments all fall within the specified range between 8.3-12.3 as indicated in FIG. 26A. Therefore, with a given ball lens diameter (or a given glass spacer length) and the specified range of ratio x based on the simplified simulation method mentioned above (i.e., following Equation 1-Equation 3), a lens designer can find an approximated range of glass spacer length (or ball lens diameter) as the initial design range for ball lens probes before optimization. This process advantageously reduces the time necessary for searching a range in the optimization process and also provides a good estimation within a tolerance range of the glass spacer for a given ball lens diameter, and vice versa.

FIG. 26B and FIG. 26C conceptualized graphs of a relation of beam profile as a function of beam propagation distance. FIG. 26B could be considered as a combination of either FIGS. 23 and 24 or FIGS. 27 and 28. As shown in this conceptualized FIG. 26B, the beam profile in the lateral direction (represented by line A) and in the longitudinal direction (represented by line B) still show certain divergence as the beam propagates away from the probe. In other words, a certain degree of astigmatism still remains. However, as shown in FIG. 26C, the shape of the beam spot is controlled such that the beam profile in the lateral direction (value of A) and in the longitudinal direction (value of B) remains substantially the same. More specifically, the inventor herein has identified that by bringing the foci of the two orthogonal directions close enough so that the beam will not be significantly diverging in one direction while the other direction is converging, image degradation can be suppressed and the optical design of the probe can be simplified. This is achieved, by optimizing the beam profile in lateral (scanning) direction more than in longitudinal (pull-back) direction while controlling the astigmatism such that the image quality of OCT is not limited by the resolution of the distal optics throughout most ranges of OCT imaging depths.

Figure 29A:
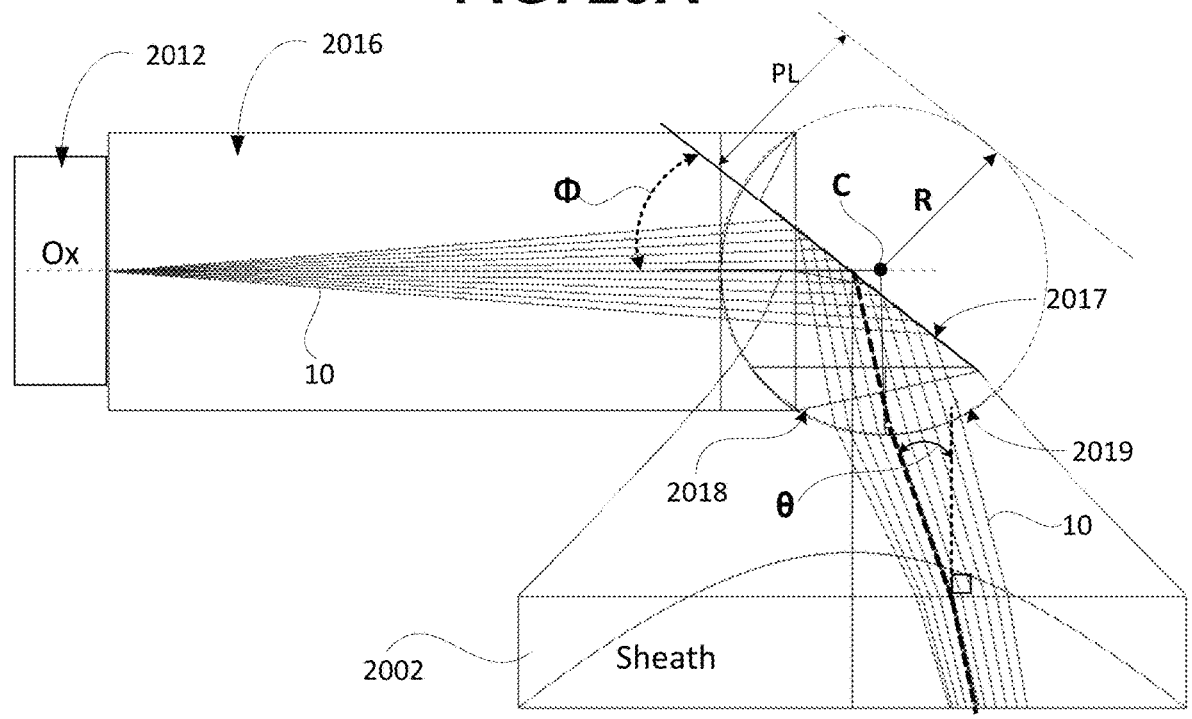
FIG. 29A shows an exemplary ray-tracing simulation for an exemplary ball lens design.

FIG. 29A illustrates an example of ray-tracing optimization used to obtain the appropriate dimensions of a spacer 2016 and/or ball lens 2018. In FIG. 29A, the ray-tracing simulation assumes a fiber 2012, a spacer 2016, and a ball lens 2018 are arranged in this order along a probe optical axis Ox. The ball lens includes an angled surface 2017 and a curved surface 2019. The angled surface 2017 is oriented at an angle phi with respect to the optical axis Ox. Curved surface 2019 is a part of a sphere having its center C aligned with the optical axis Ox. The curved surface 2019 has a radius of curvature R. The fiber 2012 delivers a light beam 10 (or other electromagnetic radiation) to the spacer 2016. The light is reflected off of the angled surface 2017 towards the curved surface 2019 of the ball lens 2018. The reflected light is focused by the curved surface 2019 at a working distance with a predetermined beam waist profile in a lateral direction and in a longitudinal direction. When measured perpendicularly from the optical axis, a beam waist location in the lateral direction is further than a beam waist location in the longitudinal direction, but the beam waist profile is substantially the same in both the lateral and longitudinal directions. To that end, according to FIG. 29A, light emits from the distal end of fiber 2012, which is a waveguide such as a single mode fiber, a multimode fiber or a double clad fiber, and passes through the spacer 2016 without undergoing any focusing or reflection. At the distal end of the spacer 2016, a ball lens 2018 is formed by fusion splicing from the spacer 2016 or being separately attached to the spacer 2016. The ball lens 2018 is then angle polished by a polishing length (P1) at 0 degrees such that the incident angle of light beam 10 to the sheath 2002 is $\ominus$ degrees. In some embodiments, as shown in FIG. 29A, the ball is over polished meaning the polishing line (interface) of angle surface 2017 passes the center C of the ball lens 2018. In other embodiments, the ball may be under polished such that the polishing length P1<R. The angled surface 2017 is a reflective surface that directs the light to the side of the probe (e.g., for side-view imaging). The reflected light beam 10 then transmits through the curved surface 2019 of the ball lens 2018, passes through the sheath 2002, and focuses on a sample (e.g., tissue) at a working distance. In the foregoing embodiments, the light beam 10 is focused by the curved surface 2019 of the ball lens 2018. The angled surface 2017 can be flat (no optical power), or it can have asymmetrical optical power (e.g., being a concave or convex cylindrical surface) to correct for residual astigmatism.

Figure 29B:
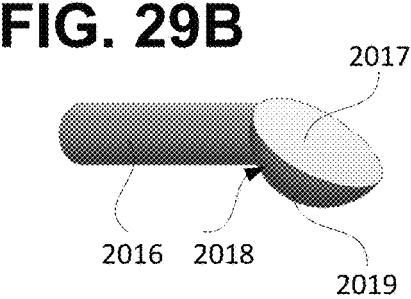
FIG. 29B, FIG. 29C, and FIG. 29D show various views of a ball lens design.
Figure 29C:
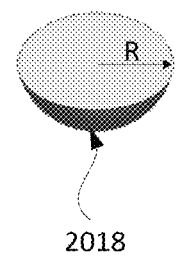
Figure 29D:
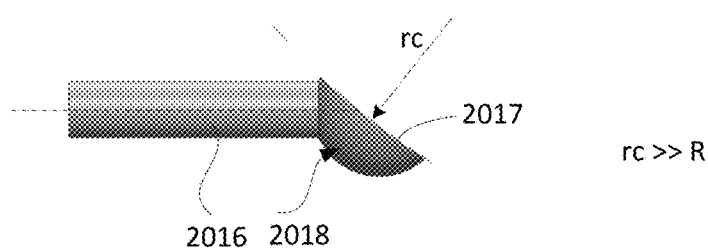

FIG. 29B, FIG. 29C, and FIG. 29D illustrated various views of a ball lens design where the angled surface 2017 has an asymmetric optical power. FIG. 29B shows a perspective view of the spacer 2016 (second light guiding component) and the ball lens 2018 formed as a monolithic piece of fused silica. FIG. 29C shows a perspective view of the polished ball lens with a radius R. FIG. 29D shows a side-view of the spacer 2018 and the balls lens 2018 where the angled surface 2017 has an asymmetric optical power. Specifically, the angled surface 2017 shown in FIG. 29D has a concave curvature in the longitudinal direction. The curvature of angled surface 2017 has a radius of curvature rc, such that rc is much larger than the radius R of the ball lens (i.e., re>>R). Here, it is noted that the FIGS. 29B-29D are merely showing the concept of an angled surface 2017 having an asymmetric optical power. In a real design, the real curvature on the reflective surface would be too small to tell that it is actually curved.

Table 19 shows a summary of the acceptable length range of glass spacer for given ball lens diameters and performance requirement.

|  | $6^{th}$ embodiment | $8^{th}$ embodiment | $10^{th}$ embodiment | $12^{th}$ embodiment | $14^{th}$ embodiment |
| --- | --- | --- | --- | --- | --- |
| Ball diameter [μm] | 300 | 310 | 320 | 330 | 340 |
| Glass spacer length [μm] | 500-800 | 550-830 | 570-850 | 600-1000 | 750-1050 |
| Ratio x | 8.89-12.22 | 8.95-11.86 | 8.69-11.43 | 8.54-12.21 | 9.43-12.02 |

Figure 27:
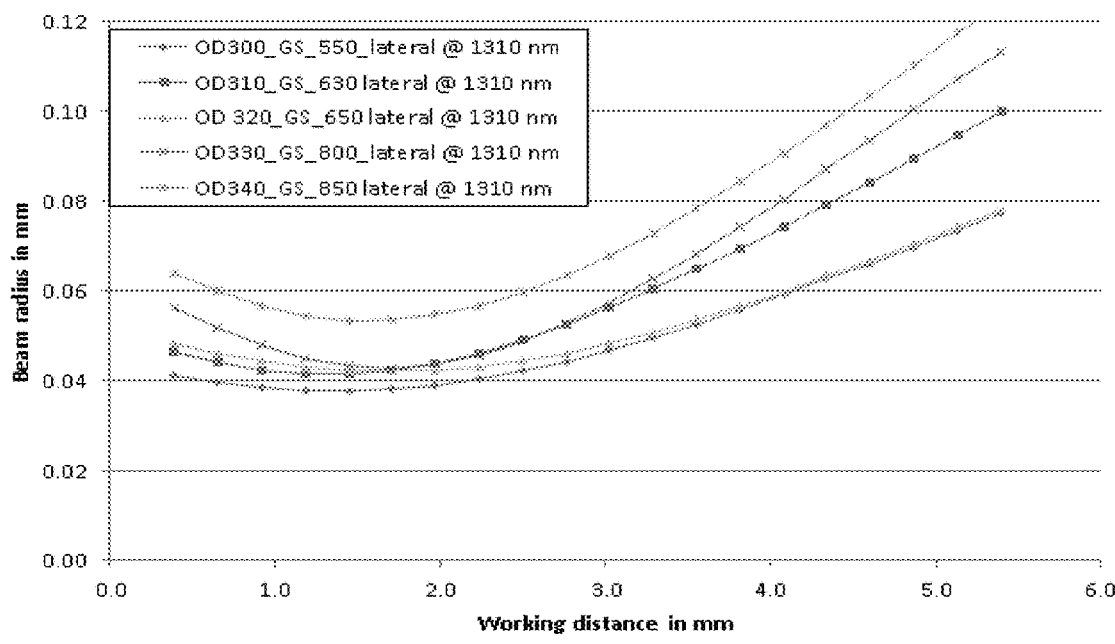
FIG. 27 is a graph showing a summary of beam profiles in lateral direction of different ball lens designs (in contrast agent with sheath) with similar ratio x.

Table 20 summarizes glass spacer lengths for different ball lens diameters from $5^{th}$, $7^{th}$, $9^{th}$, $11^{th}$ and $13^{th}$ embodiments. These embodiments are the exemplary results of further optimization within the ranges of glass spacer length of different ball lens diameters. The beam profiles in lateral direction and longitudinal direction for each design is simulated by Physical Wave Propagation Model and summarized in FIG. 27 and FIG. 28, respectively. During final optimization process, more accurate model such as Physical Wave Propagation is recommended and is used in this disclosure to achieve more accurate prediction in the beam performance. Thus the numerical values for beam waist location in FIG. 27 are different from the results shown in FIG. 25, which is based on Gaussian beam approximation with the modified lens formula. This discrepancy can be understood from the fact that, as discussed above, Gaussian beam approximation is less accurate than Physical Wave Propagation model.

Figure 28:
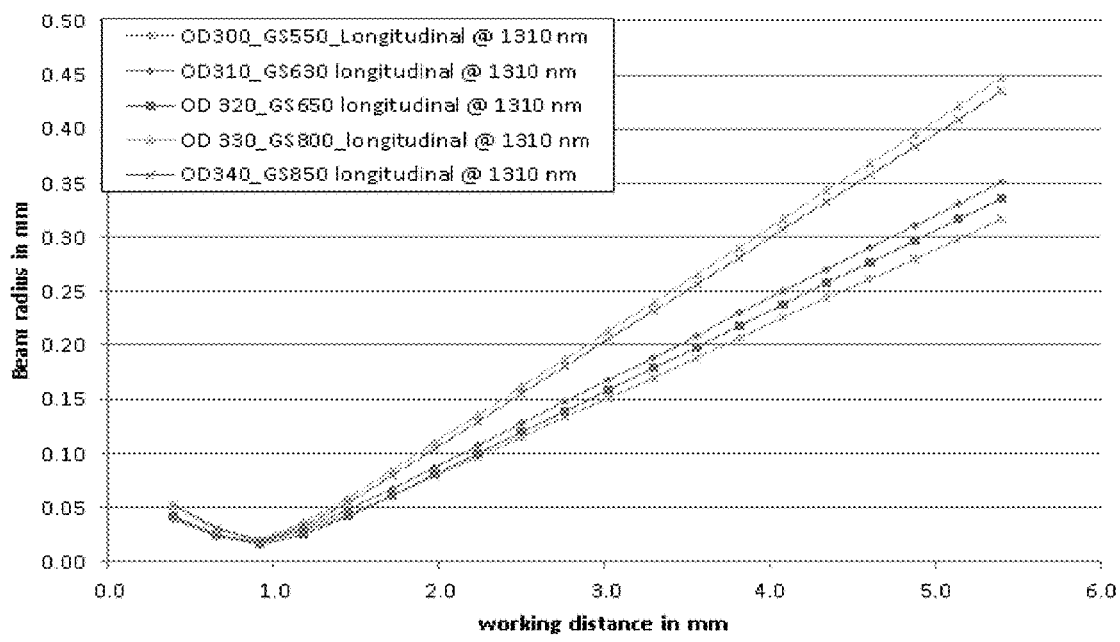
FIG. 28 is a graph showing a summary of beam profiles in longitudinal direction of different ball lens designs (in contrast agent with sheath) with similar ratio x.

From the summarized results in Table 20, and the plots shown in FIG. 27 and FIG. 28, it is evident that using the "ratio x" defined in Equation 3 in a predefined numerical range of between 8.3 and 12.3, similar beam performance (e.g., similar beam waist locations and divergence angles) of different ball lens designs (i.e. different ball lens diameter and glass spacer length) can be achieved. Here, it should be understood that the exemplary results of all embodiments in the present disclosure are based on other design parameters including sheath radii, materials of sheath, ball lens, $2^{nd}$ light guiding component (glass spacer) being fixed to the numerical values listed in Table 3. If any of those parameters are changed, the values and the ranges listed in Table 19 and Table 20 would change accordingly. In addition it is noted that the sampling spacing of working distance in beam profile simulation is 0.25 mm.

Table 20 summarizes glass spacer lengths for a given ball lens diameter

|  | $5^{th}$ embodiment | $7^{th}$ embodiment | $9^{th}$ embodiment | $11^{th}$ embodiment | $13^{th}$ embodiment |
|---|---|---|---|---|---|
| Ball diameter [μm] | 300 | 310 | 320 | 330 | 340 |
| Glass spacer length [μm] | 550 | 630 | 650 | 800 | 850 |
| Ratio x [1/mm] | 9.44 | 9.78 | 9.47 | 10.38 | 10.29 |
| Beam waist location in lateral direction [mm] | 1.5 | 1.5 | 1.75 | 1.75 | 1.5 |
| Beam waist location in longitudinal direction [mm] | 0.92 | 0.92 | 0.92 | 0.92 | 0.92 |

Table 21 summarizes optical probe parameters for a specific example

| Optical specs for a specific example of an optical probe Beam Waist profile | | |
|---|---|---|
| Divergence φ in air without sheath @ 1310 nm | in lateral direction | Nominal 0.08 (0.055 < φ < 0.12 rad) |
| | in longitudinal direction | Nominal 0.082 (0.055 < φ < 0.12 rad) |
| Divergence φ in contrast agent with sheath @ 1310 nm | in lateral direction | Nominal 0.015 (0.01 < φ < 0.026 rad) |
| | in longitudinal direction | φ < 0.08 rad |
| Beam waist* in air without sheath (waist location**, radius) | in lateral direction | (waist position 0.7 +/− 0.3 mm, beam radius ~12 μm) |
| | in longitudinal direction | |
| Beam waist* in contrast with sheath (waist location**, radius) | in lateral direction | (waist position > 1.2 mm, beam radius ~35 μm) |
| | in longitudinal direction | (waist position > 0.8 mm, beam radius ~16 μm) |
| Incident angle to sheath in air | in longitudinal direction | θ = 19.6 +/− 3 degrees |
| Return loss | | <−60 dB @ 1310 nm +/− 20 nm |
| Transmittance | | >95% @ 1310 nm +/− 20 nm |
| Ball lens | diameter [μm] | 300 +/− 5 |
| | polish angle [degrees] | Ø = 38 +/− 2 |
| | polish length [μm] | 170 +/− 10 |
| Spacer | diameter [μm] | 125 or 250 (preferred) +/− 10 μm |
| | Total length (spacer length + ball diameter) | 850 +/− 30 μm (550 spacer length + 300 ball diameter) |
| | connection to DCF | Splice |
| Fiber | Double clad fiber (DCF) | Protective low index epoxy (MY136) over the stripped fiber |
| | interface | Epoxy filled the gap edge between fiber, spacer and ball lens |
| Probe assembly | probe total length [mm] | 1800 +/− 20 |
| | Connector | None |
| Sheath | inner diameter [μm] | 584 +/− 12.7 |
| | wall thickness [μm] | 95 +/− 12.7 |
| | Refractive index @ 1310 nm | 1.5 |

*Beam waist profile defined by 1/e^2 @ 1310 nm
**Beam waist location is measured perpendicularly from optical axis of double clad fiber and glass spacer with asymmetric optical power to compensate the asymmetric optical power from the sheath.

In addition, the proposed design method to search for appropriate length of the second light guiding component (e.g., glass spacer length) with a certain ball lens diameter so as to balance astigmatism of the beams in two orthogonal directions without adding additional optical component with asymmetric optical power provides the benefit of faster prototyping and modeling new optical probes.

Proposed design method to search for appropriate length of 2nd light guiding component (ex. glass spacer length)

The foregoing embodiments and examples bring about significant advantages over known OCT optical probe design. Among those advantages, the disclosed ball lens designs provide optical probes with balanced astigmatism and substantially achromatic performance between 633±10 nm and 1310 nm which is considered to be of significant benefit for MMOCT imaging. Specifically, the image quality is improved in a multimodality OCT system by using such probe designs without adding additional optical components with a certain ball lens diameter so as to achromatize the beams between 633±10 nm and 1310 nm without adding additional optical component.

Further, the proposed design method to search for appropriate length range of second light guiding component (ex. glass spacer length) with a certain ball lens diameter that meets performance specification by using the ratio x defined in equation 3 reduces the search range of glass spacer length and ball lens diameter to achieve the desired performance.

With the disclosed optical probe having a ball lens and first and second light guiding components, "balanced astigmatism" in the distal optics design for OCT imaging is achieved. To balance astigmatism, the disclosed optical probes take advantage of different sampling sizes in OCT imaging and optimize the beam profile in lateral (scanning) direction more than in longitudinal (pull-back) direction while controlling the astigmatism caused by sheath such that the image quality of OCT is not limited by the resolution of the distal optics throughout the full range of OCT imaging depth.

For a multi modality OCT probe (MMOCT probe), the disclosed optical probe designs achieve "balanced astigmatism" and achromatic distal optics for OCT and fluorescence imaging. Not only because of different sampling sizes in OCT imaging but also because of different NA requirements between excitation and detection for fluorescence imaging, astigmatism is allowed to be present in the probe system but needs to be controlled. According to the present disclosure, one of optimization objectives is to have smaller NA and farther beam waist location in lateral direction than in longitudinal direction, while allowing larger NA and closer beam waist location for both OCT and fluorescence imaging.

The ball lens probe is made with an angled surface such that incident angle θ to the normal of the inner surface of the sheath is in the range of 10-25 degrees. In some embodiments, the incident angle θ is at 20 degrees±4 degrees when the inner medium is air. In an embodiment, the angled surface is made by angle polishing the ball lens. In other embodiments, the angled surface is made by other methods such as 3D printing the ball lens together or separately with the second light guiding component.

The polishing angle Φ (indicated in FIG. 2B) is in the range of 35 to 41 degrees. In some preferred embodiments, the polishing angle is at 38±1 degrees. The polishing length of the ball lens is slightly over or under the radius of the ball lens to reduce the back-reflection from the angled surface. In some preferred embodiments, the ratio of the ball radius and the (polishing) length (i.e. (ball radius)/(polishing length)) is in the range of 0.85-0.95 for over polishing and is between 1.05-1.18 for under polishing.

The sheath has an inner diameter in the range of 500 μm-650 μm, an outer diameter in the range of 700-850 μm and a refractive index of about 1.5. In some preferred embodiments, the sheath has an inner diameter of 584±12.7 μm and an outer diameter of 787±12.7 μm. The outer medium of the sheath is contrast agent and the inner medium is air.

The ball lens diameter ranges that is suitable for such ball lens probe configuration listed in Table 3 ranges from 290 μm-350 μm assuming the ball lens is made of fused silica.

The exemplary designs of an optical probe having a first light guiding component, a second light guiding component, a ball lens at the distal end thereof are based on the parameters listed in Table 3. However, the various designs are not limited to fixed parameters of Table 3. Once the parameters in Table 3 are changed, the design values for ball lens diameter, polishing length and spacer length should be adjusted to meet the optical specification of Table 3 based on the same design methods described through this disclosure.

An exemplary OCT system has the following operational parameters: 500 A lines per frame; 40 mm/s pull back speed with 200 fps. The sampling size is 0-63 um for an imaging depth from 0-5 mm in lateral/scanning direction, and is about 200 μm in pull back movement in longitudinal direction.

[OCT/Fluorescence Multi-Modality System]

Figure 31A:
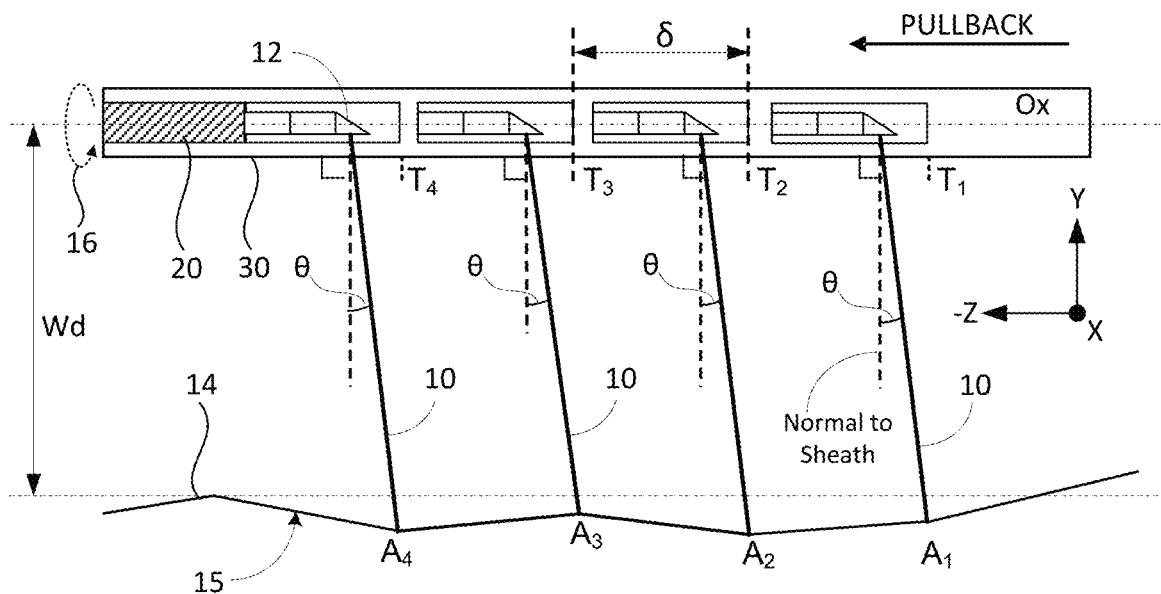
FIG. 31A and FIG. 31B respectively illustrate transverse and axial views of conventional distal optics (optical probe) of a catheter at sequential positions during a pullback operation.
Figure 31B:
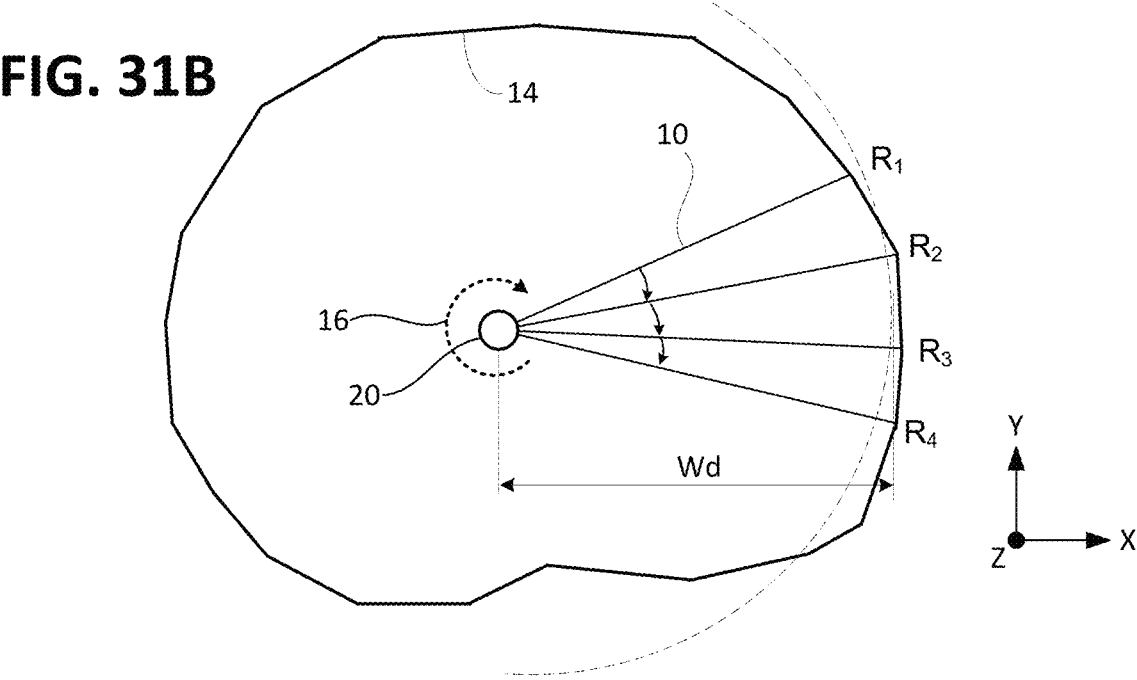
Figure 32A:
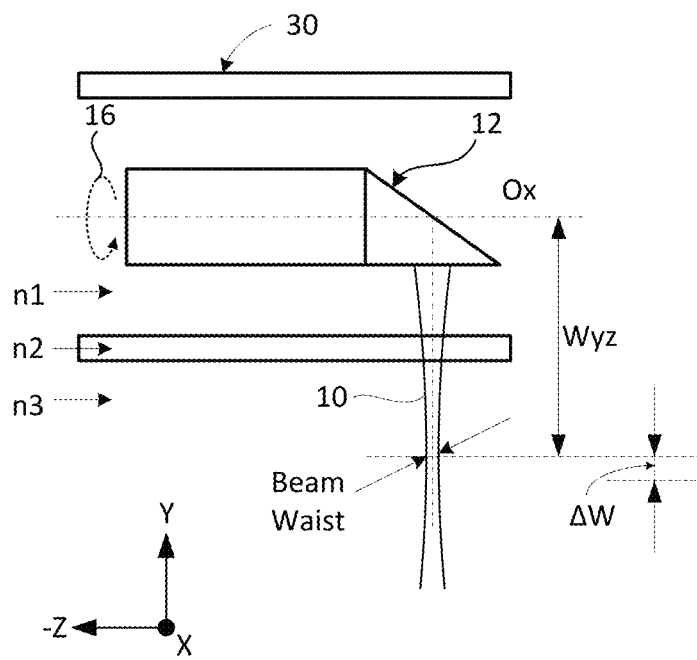
FIG. 32A and FIG. 32B respectively illustrate transverse (longitudinal) and axial (lateral) views of conventional distal optics (optical probe) of a catheter with the focusing effect caused by the tubular shape of the sheath 102.
Figure 32B:
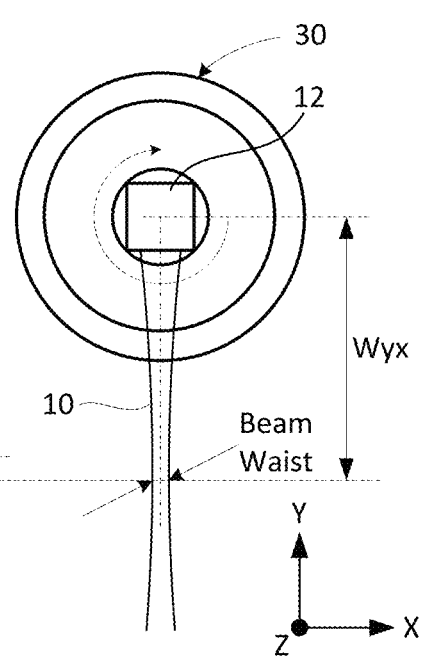
Figure 32C:
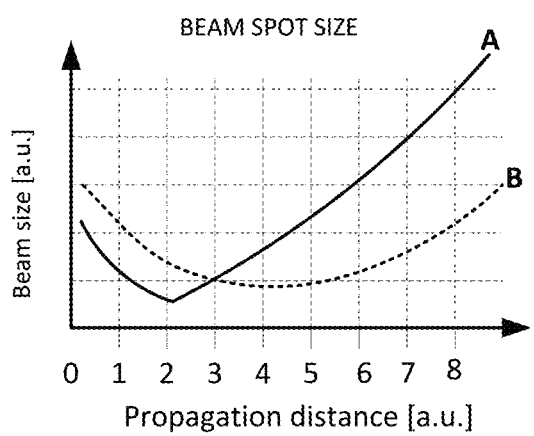
FIGS. 32C and 32D show exemplary graphs of the irradiance profile of an astigmatic beam.
Figure 32D:
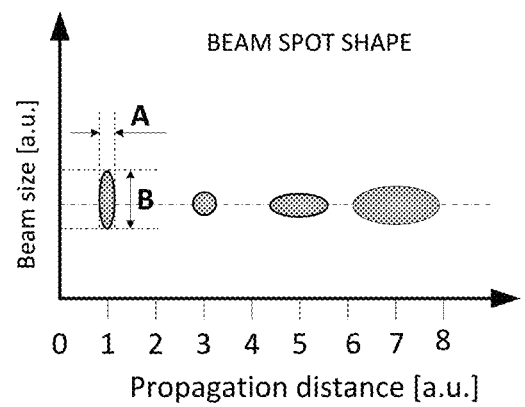

FIG. 31 illustrates an exemplary system 100 including an interferometric OCT modality and a fluorescence modality that can be applied as an intravascular OCT-NIRAF system for imaging of coronary arteries or other bodily lumens. As depicted in FIG. 31, the system 100 may includes an OCT modality comprised of interferometer having a sample arm and a reference arm, a light source 110, a detector unit 120, data acquisition electronics 130, and a computer 190. The sample arm includes a patient interface unit (PIU) 150 and a catheter 160. In addition, the system 100 includes a NIRAF/NIRF modality comprised of a light source 810 also connected to the catheter 160 via a fiber 811, and to computer 190 via the PIU 150. In one embodiment, the system 100 may use a swept-source laser (1310 nm+/−50 nm) as the OCT light source, and a 633 nm HeNe laser as the excitation light source for fluorescence excitation. The distal optics of the catheter 160 includes a double clad fiber (DCF) with a polished ball lens at the tip thereof for side-view imaging. The distal optics of the MMOCT system 100 are implemented according to the imaging catheter design shown in FIG. 1A and FIG. 1B, and according to the ball lens optical probe design shown in FIGS. 2A and 2B In this manner with this exemplary MMOCT system 100, OCT and NIRAF data can be obtained simultaneously.

In the MMOCT system 100, light (radiation of first wavelength) from the light source 110 is guided through the sample arm to a sample 170, and through the reference arm to a reflector 140, to thereby generate OCT interference patterns. Specifically, light from the light source 110 is split by a splitter 102 (fiber splitter or beam splitter) into a sample beam and a reference beam which are respectively conveyed to the sample arm and the reference arm via respective optical fibers. In the sample arm, the sample beam enters a circulator 105, passes to a fiber coupler 108 via a single-mode (SM) fiber 106, and the sample beam is delivered to the catheter 160 via a double clad fiber 107a. The proximal end of catheter 160 is connected to the PIU 160, and the PIU 160 is in turn connected to computer 190. Under control of the computer 190, the PIU 160 controls the sample beam to irradiate the sample 170 in a scanning manner. Light of the sample beam reflected and/or scattered by the sample 170 is collected by optics 3010 (an optical probe according to any of the embodiments described above) arranged at the distal end of the catheter 160, and the collected light is transmitted back through a double clad fiber 107b to the PIU 150 and to fiber coupler o18. The fiber coupler o18 couples one part of the sample beam towards the circulator 105 via the SM fiber 106; and the circulator 105 guides the one part of the sample beam to the combiner 104. In addition, the fiber coupler 108 couples another part of the sample beam to a second detector 122 (second detector) via a multi-mode fiber 109.

In the reference arm, light of the reference beam enters a circulator 103 and is delivered to the reflector 140 via a non-labeled optical fiber. In the case of Time Domain OCT imaging, the reflector 140 may be implemented as a scanning mirror. And, in the case of Frequency Domain OCT (FD-OCT) imaging, the reflector 140 may be implemented as a stationary mirror. Light of the reference beam reflected from the reflector 140 passes through the circulator 105, and is also guided to the combiner 104. In this manner, the sample and reference beams are combined at the beam combiner 104 and then detected by detector 121 to generate interference signals according to known OCT principles.

The output of the interferometer (interference patterns) is detected by the detector 121 (first detector). The first detector 121 is implemented as an array of photodiodes, a photo multiplier tube (PMT), a multi-array of cameras or other similar interference pattern detecting device. The signals output from the first detector 121 are pre-processed by data acquisition electronics (DAQ1) 131, and transferred to a computer 190. The computer 190 performs signal processing to generate OCT images in a known manner. The interference patterns are generated only when the path length of the sample arm matches the path length of the reference arm within the coherence length of the light source 110.

In the NIRAF/NIRF modality, an excitation light with a wavelength of 633 nm (radiation of second wavelength) from a second light source 810 irradiates the sample 170 through the PIU 150 and the distal optics of catheter 160. The sample 170 emits a near infrared auto-fluorescence signal (NIRAF signal) or near infrared fluorescence signal (NIRF signal) with broadband wavelengths of about 633 to 800 nm (radiation of third wavelength), in response to being irradiated by the excitation light. The auto-fluorescence (or fluorescence) light is collected by the distal optics of the catheter 160 and delivered back to a third detector 833 (DET3) via an optical fiber 819 which is connected to the PIU 150. The signal (fluorescence intensity signal) output from detector 833 is digitized by data acquisition electronics 132 (DAQ2) and transmitted to computer 190 for image processing.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like. An I/O interface can be used to provide communication interfaces to input and output devices, which may include a keyboard, a display, a mouse, a touch screen, touchless interface (e.g., a gesture recognition device) a printing device, a light pen, an optical storage device, a scanner, a microphone, a camera, a drive, communication cable and a network (either wired or wireless).

The detector interface also provides communication interfaces to input and output devices. The detector may include, for example a photomultiplier tube (PMT), a photodiode, an avalanche photodiode detector (APD), a charge-coupled device (CCD), multi-pixel photon counters (MPPC), or other. Also, the function of detector may be realized by computer executable instructions (e.g., one or more programs) recorded on a Storage/RAM.

Definitions

In referring to the description, specific details are set forth in order to provide a thorough understanding of the examples disclosed. In other instances, well-known methods, procedures, components and circuits have not been described in detail as not to unnecessarily lengthen the present disclosure. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", may be abbreviated as "/", and it includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about" or "approximately" as used herein means, for example, within 10%, within 5%, or less. In some embodiments, the term "about" may mean within measurement error or tolerance. In this regard, where described or claimed, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range, if recited herein, is intended to include all sub-ranges subsumed therein. As used herein, the term "substantially" is meant to allow for deviations from the descriptor that do not negatively affect the intended purpose. For example, deviations that are from limitations in measurements, differences within manufacture tolerance, or variations of less than 5% can be considered within the scope of substantially the same. The specified descriptor can be an absolute value (e.g. substantially spherical, substantially perpendicular, etc.) or a relative term (e.g. substantially not differing beam waist profile, substantially at the same time, etc.).

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", "said" and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated. It is further noted that some claims may be drafted to exclude any optional element; such claims may use exclusive terminology as "solely," "only" and the like in connection with the recitation of claim elements, or it may use of a "negative" limitation.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

The invention claimed is:

1. An optical probe, comprising:
a first light guiding component; a second light guiding component; and a ball lens arranged in this order from a proximal end to a distal end and along an optical axis of the probe,
wherein the probe is configured to transmit at least two light beams including a first beam having a first wavelength and a second beam having a second wavelength different from the first wavelength,
wherein the ball lens has a curved surface and an angled surface arranged such that light traveling from the proximal end to the distal end is reflected off from the angled surface towards the curved surface, and the curved surface focuses the light at a working distance with a beam waist profile having lateral and longitudinal directions,
wherein, when measured perpendicularly from the optical axis, a beam waist location of the first beam is different than a beam waist of the second beam, and
wherein the beam waist profile of the first and second beams in the lateral direction differs less than the beam waist profile in the longitudinal direction.

2. The optical probe according to claim 1,
wherein the angled surface reflects the light towards the curved surface by total internal reflection and/or by a mirror coating on the angled surface.

3. The optical probe according to claim 1,
wherein the probe focuses the first and second beams such that the beam waist locations between the first beam having the first wavelength and the second beam having the second wavelength are within a substantially fixed difference in a working distance range of 0.5 to 5.0 mm along the lateral direction.

4. The optical probe according to claim 1,
wherein the probe focuses the first and second beams such that the beam waist locations between the first beam having the first wavelength and the second beam having the second wavelength increasingly differ from each other in a working distance range of 0.5 to 5.0 mm along the longitudinal direction.

5. The optical probe according to claim 1,
wherein the first beam has OCT wavelength for OCT imaging and the second beam has fluorescence excitation wavelength for fluorescence imaging, and
wherein probe is substantially achromatic such that the beam waist locations between the beam having OCT wavelength and the beam having fluorescence excitation wavelength are within a substantially fixed difference in a working distance range of 0.5 to 5.0 mm along the lateral direction.

6. The optical probe according to claim 1, further comprising a sheath surrounding the probe, the sheath having an asymmetric optical power in lateral and longitudinal directions,
wherein the first beam has a wavelength of 633±10 nm and the second beam has a wavelength of 1310 nm, and
wherein the ball lens is configured to provide balanced astigmatism and substantially achromatic performance between the first and second beams without adding an additional optical component with asymmetric optical power to compensate for the asymmetric optical power of the sheath.

7. The optical probe according to claim 6,
wherein the curved surface focuses the light onto an inner surface of the sheath at an incident angle, and
wherein the incident angle to the normal of the inner surface of the sheath is in a range of 10 to 25 degrees.

8. The optical probe according to claim 7, wherein the incident angle is at 20±4 degrees when a medium surrounding the optical probe is air.

9. The optical probe according to claim 1,
wherein the ball lens has a substantially spherical shape and the sphere is made of fused silica having its center aligned with the optical axis of the probe,
wherein the curved surface of the ball lens is a first part of the sphere and the angled surface is formed by polishing a second part of the sphere, and
wherein the angled surface intersects the optical axis at an angle between 35 and 41 degrees inclusive.

10. The optical probe according to claim 9, wherein the angled surface intersects the optical axis at an angle in a range of 35 to 41 degrees.

11. The optical probe according to claim 9, wherein the angled surface intersects the optical axis at an angle of 38±1 degrees.

12. The optical probe according to claim 9, wherein a ratio of the radius of the sphere to a polishing length of the second part of the sphere, defined as (ball lens radius)/(polishing length), is in a range from 0.85 to 0.95 or in a range from 1.05 to 1.18.

13. The optical probe according to claim 9, wherein a total length of the length of the second light guiding component defined as (second light guiding component length) plus the ball lens diameter defined as (ball lens diameter) measured along the optical axis is proportional to an effective focal length of the curved surface.

14. The optical probe according to claim 13, wherein the following ratio x holds in a range of 8.3 to 12.3 [1/mm], where $$x = (\text{second light guiding component length} + \text{ball lens diameter})/(\text{ball lens diameter})^2.$$

15. The optical probe according to claim 14,
wherein the ball lens diameter ranges from 290 μm to 350 μm, and
wherein the second light guiding component length ranges from 500 μm to 1050 μm.

16. The optical probe according to claim 1,
wherein the first light guiding component includes a single mode fiber, a double clad fiber, or a multimode fiber,
wherein the second light guiding component includes a fused silica glass spacer, a coreless fiber, or cylindrical rod made of optical grade polymers, and
wherein the ball lens is formed by a fusion lens forming procedure from the second light guiding component, and the angled surface is formed by polishing a distal end part of the ball lens.

17. The optical probe according to claim 1,
wherein the angled surface has substantially no optical power in any of the lateral or longitudinal directions.

18. The optical probe according to claim 1,
wherein the angled surface has a positive optical power in at least one of the lateral or longitudinal directions.

19. The optical probe according to claim 1,
wherein the angled surface has asymmetric optical power and the optical power in the longitudinal direction is positive.

20. An imaging apparatus for multi-modality optical coherence tomography (MMOCT) imaging of a bodily lumen, comprising:
an optical probe including a first light guiding component, a second light guiding component, and a focusing component arranged in this order from a proximal end to a distal end along an optical axis of the probe; and
a sheath surrounding at least the distal end of the probe,
wherein the probe is configured to transmit at least two light beams having different wavelengths from each other and to collect light with at least two different wavelength ranges through the sheath,
wherein the focusing component includes a focusing surface and a reflecting surface, the reflecting surface is oriented at an angle with respect to the optical axis such that light traveling from the proximal end to the distal end is reflected from the reflecting surface towards the focusing surface, and the focusing surface focuses the light at a working distance with a beam waist profile having lateral and longitudinal directions,
wherein, when measured perpendicularly from the optical axis, a beam waist location of the first beam differs from a beam waist location of the second beam in proportion to the lateral and longitudinal directions, and
wherein the beam waist location of the first and second beams in the lateral direction differs less than the beam waist location in the longitudinal direction along the working distance.

21. The imaging apparatus according to claim 20,
wherein the focusing component is a ball lens coupled to the distal end of the second light guiding component,
wherein the ball lens is integrally formed with the second light guiding component by a fusion lens forming procedure from the second light guiding component, and
wherein the reflecting surface of the focusing component is an angle polished surface made by angle polishing a distal end part of the ball lens.

22. The imaging apparatus according to claim 20,
wherein the at least two light beams include a first beam having OCT wavelength for OCT imaging and a second beam having fluorescence excitation wavelength for fluorescence imaging, and
wherein the beam waist locations between the beam having OCT wavelength and the beam having fluorescence excitation wavelength differ by approximately 3 mm in the lateral direction within a working distance range of 0.5 to 5.0 mm.

23. The imaging apparatus according to claim 21,
wherein the at least two light beams include a first beam having a wavelength of 633±10 nm and a second beam having a wavelength of 1310 nm,
wherein the sheath has an asymmetric optical power in the lateral and longitudinal directions, and
wherein the ball lens is configured to provide balanced astigmatism and substantially achromatic performance the first and second beams without adding an additional optical component with asymmetric optical power to compensate for the asymmetric optical power of the sheath.

24. The imaging apparatus according to claim 21, wherein the reflecting surface reflects the light towards the curved surface by total internal reflection and/or by a mirror coating on the angled surface.

25. The imaging apparatus according to claim 24, wherein the curved surface of the ball lens guides the reflected light through an inner surface of the sheath at an incident angle such that the incident angle to the normal of the inner surface of the sheath is in a range of 10-25 degrees.

26. The imaging apparatus according to claim 20,
wherein the ball lens has a substantially spherical shape and the sphere is made of fused silica having its center aligned with the optical axis of the probe,
wherein the curved surface of the ball lens is a first part of the sphere and the angled surface is formed by polishing a second part of the sphere, and
wherein the angled surface intersects the optical axis at an angle between 35 and 41 degrees inclusive.

27. The imaging apparatus according to claim 26, wherein a ratio of the radius of the sphere to a polishing length of the second part of the sphere defined as (ball lens radius)/(polishing length) is in a range from 0.85 to 0.95 or in a range from 1.05 to 1.18.

28. The imaging apparatus according to claim 26, wherein a total length of the length of the second light guiding component (second light guiding component length) plus the ball lens diameter measured along the optical axis is proportional to an effective focal length of the curved surface.

29. The imaging apparatus according to claim 28, wherein the following ratio x holds in a range of 8.3 to 12.3 [1/mm], where $x$=(second light guiding component length+ball lens diameter)/(ball lens diameter)$^2$.

30. The imaging apparatus according to claim 28, wherein the ball lens diameter ranges from 290 μm to 350 μm, and
wherein the second light guiding component length ranges from 500 μm to 1050 μm.
31. The imaging apparatus according to claim 20, wherein the angled surface has no optical power in any of the lateral or longitudinal directions.
32. The imaging apparatus according to claim 20, wherein the angled surface has a positive optical power in at least one of the lateral or longitudinal directions.
33. The imaging apparatus according to claim 20, wherein the angled surface has asymmetric optical power and the optical power in the longitudinal direction is positive.

* * * * *